US011200968B2

(12) United States Patent
Kartoun et al.

(10) Patent No.: US 11,200,968 B2
(45) Date of Patent: Dec. 14, 2021

(54) VERIFYING MEDICAL CONDITIONS OF PATIENTS IN ELECTRONIC MEDICAL RECORDS

(71) Applicant: International Business Machines Corporation, Armonk, NY (US)

(72) Inventors: Uri Kartoun, Cambridge, MA (US); Kenney Ng, Arlington, MA (US)

(73) Assignee: International Business Machines Corporation, Armonk, NY (US)

( * ) Notice: Subject to any disclaimer, the term of this patent is extended or adjusted under 35 U.S.C. 154(b) by 753 days.

(21) Appl. No.: 15/849,255

(22) Filed: Dec. 20, 2017

(65) Prior Publication Data
US 2019/0189253 A1 Jun. 20, 2019

(51) Int. Cl.
| | | |
|---|---|---|
| *G16H 50/30* | (2018.01) | |
| *G16H 10/60* | (2018.01) | |
| *G16H 50/70* | (2018.01) | |
| *G16H 15/00* | (2018.01) | |
| *G16H 20/00* | (2018.01) | |
| *G16H 40/63* | (2018.01) | |

(Continued)

(52) U.S. Cl.
CPC ............ *G16H 10/60* (2018.01); *G16H 15/00* (2018.01); *G16H 20/00* (2018.01); *G16H 40/63* (2018.01); *G16H 50/20* (2018.01); *G16H 50/30* (2018.01); *G16H 50/70* (2018.01); *G16H 70/20* (2018.01)

(58) Field of Classification Search
CPC ........ G16H 10/60; G16H 15/00; G16H 50/30; G16H 50/70; G16H 50/20; G16H 20/00; G16H 40/63; G16H 70/20; G06F 19/00; G06F 17/30; G06Q 50/00

USPC .......................................................... 705/2, 3
See application file for complete search history.

(56) References Cited

U.S. PATENT DOCUMENTS 8,260,637 B2  9/2012  Kochendorfer et al.
9,519,885 B2  12/2016  Kochendorfer et al.
(Continued)

OTHER PUBLICATIONS

"The Era of Cognitive Systems: An inside look at IBM Watson and how it works", IBM Corporation, IBM Software Group, Whitepaper, IBM Watson Solutions, Sep. 2012, 19 pages.
(Continued)

*Primary Examiner* — Jonathan Durant
*Assistant Examiner* — Alaaeldin M Elshaer
(74) *Attorney, Agent, or Firm* — Stephen J. Walder, Jr.; William J. Stock

(57) ABSTRACT

Mechanisms are provided to implement a medical condition verification system. The medical condition verification system receives patient electronic medical record (EMR) data and parses the patient EMR data to identify an instance of a medical code or medical condition indicator present in the patient EMR data. The medical condition verification system performs cognitive analysis of the patient EMR data to identify evidential data supportive of the instance referencing an associated medical condition. The medical condition verification system generates a measure of risk of the patient having the medical condition based on the identified evidential data and based on a machine learned relationship of medical factors in patient EMR data relevant to generating the measure of risk for the associated medical condition. The medical condition verification system generates an output representing the measure of risk of the patient having the associated medical condition.

20 Claims, 7 Drawing Sheets

(51) Int. Cl.
  *G16H 50/20* (2018.01)
  *G16H 70/20* (2018.01)
  *A61B 5/00* (2006.01)

(56) References Cited

U.S. PATENT DOCUMENTS

| | | | |
|---|---|---|---|
| 2009/0006132 | A1 | 1/2009 | Avinash et al. |
| 2010/0094655 | A1 | 4/2010 | Kochendorfer et al. |
| 2010/0106524 | A1* | 4/2010 | Wu .................. G16H 50/30 705/3 |
| 2010/0179827 | A1* | 7/2010 | McCallie, Jr. ......... G16H 10/60 705/3 |
| 2012/0215560 | A1 | 8/2012 | Ofek et al. |
| 2012/0290319 | A1* | 11/2012 | Saria .................. G16H 10/60 705/3 |
| 2012/0310673 | A1 | 12/2012 | Kochendorfer et al. |
| 2014/0280353 | A1* | 9/2014 | Delaney ............... G06F 16/367 707/794 |
| 2015/0213224 | A1* | 7/2015 | Amarasingham ....... G06F 19/00 705/2 |
| 2015/0305688 | A1 | 10/2015 | Rath et al. |
| 2015/0347705 | A1* | 12/2015 | Simon .................. G16H 10/60 705/3 |

OTHER PUBLICATIONS

Alemzadeh, Homa et al., "An NLP-based Cognitive System for Disease Status Identification in Electronic Health Records", IEEE, 2017 IEEE EMBS International Conference on Biomedical & Health Informatics (BHI), Feb. 16-19, 2017, 4 pages.
Ananthakrishnan, Ashwin N. et al., "Improving Case Definition of Crohn's Disease and Ulcerative Colitis in Electronic Medical Records Using Natural Language Processing: A Novel Informatics Approach", Inflamm Bowel Dis. Jun. 2013; 19(7): 19 pages.
Beam, Andrew L. et al., "Predictive Modeling of Physician-Patient Dynamics that Influence Sleep Medication Prescriptions and Clinical Decision-Making", Scientific Reports, 2017: 9;7:42282, Feb. 9, 2017, 7 pages.
Blei, David M. et al., "Latent Dirichlet Allocation", Journal of Machine Learning Research 3, Jan. 2003, pp. 993-1022.
Carroll, Robert J. et al., "Portability of an algorithm to identify rheumatoid arthritis in electronic health records", J Am Med Inform Assoc. Jun. 2012;19(e1):e162-9. Epub Feb. 28, 2012, 9 pages.
Corey, Kathleen E. et al., "Development and Validation of An Algorithm to Identify Nonalcoholic Fatty Liver Disease in the Electronic Medical Record", Department of Health & Human Services, HHS Public Access, Author Manuscript, available in PMC Mar. 1, 2017; Published in final edited form as: Dig Dis Sci. Mar. 2016; 61(3): 913-919. doi: 10.1007/s10620-015-3952-x, pp. 1-14.
Corey, Kathleen E. et al., "Using an Electronic Medical Records Database to Identify Non-Traditional Cardiovascular Risk Factors in Nonalcoholic Fatty Liver Disease", The American Journal of Gastroenterology, 111 (5), Jan. 2016, 6 pages.
Deleger, Louise et al., "Building Gold Standard Corpora for Medical Natural Language Processing Tasks", Proceedings of AMIA Annual Symposium, Nov. 3, 2012, 10 pages.
Demner-Fushman, Dina et al., "What can Natural Language Processing do for Clinical Decision Support?", J Biomed Inform., Oct. 2009, 29 pages.
Griffiths, Thomas L. et al., "Finding Scientific Topics", PNAS, vol. 101, Apr. 6, 2004, pp. 5228-5235.
High, Rob, "The Era of Cognitive Systems: An Inside Look at IBM Watson and How it Works", IBM Corporation, Redbooks, Dec. 12, 2012, 16 pages.
Kartoun, Uri et al., "A Human-Robot Collaborative Reinforcement Learning Algorithm", J Intell Robot Syst (2010) 60:217-239, DOI 10.1007/s10846-010-9422-y, May 5, 2010, pp. 217-239.
Kartoun, Uri, "Text Nailing: An Efficient Human-in-the-Loop Text-Processing Method", Interactions.ACM.ORG, Interactions, Nov.-Dec. 2017, 6 pages.
Kartoun, Uri et al., "The Spectrum of Insomnia-Associated Comorbities in an Electronic Medical Records Cohort", AMIA 2016 Annual Symposium, Nov. 12-16, 2016, 2 pages.
Kartoun, Uri, "The Spectrum of Insomnia-Associated Comorbities in an Electronic Medical Records Cohort", AMIA 2016 Annual Symposium, Nov. 12-16, 2016, 29 pages.
Liao, Katherine P. et al., "Electronic Medical Records for Discovery Research in Rheumatoid Arthritis", Arthritis Care Res (Hoboken). Aug. 2010; 62(8), 17 pages.
Simon, Tracey G. et al., "Model for End-Stage Liver Disease Na Score Predicts Incident Major Cardiovascular Events in Patients with Nonalcoholic Fatty Liver Disease", Hepatology Communications, vol. 00, No. 00, 2017, 10 pages.
Suresh, Harini et al., "Clinical Intervention Prediction and Understanding using Deep networks", Proceedings of the 2nd Machine Learning for Healthcare Conference, May 2017, 16 pages.
Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

* cited by examiner

FIG. 5A

500 — [ HYPERTENSION | DIABETES ]     [ DISEASES AT RISK ] — 560

501 — NOTES FROM LAST VISIT (20 Dec 2016)

Plan
- Will increase the losartan to 100mg qd
- Continue checking home BPs 3x/wk
- Let me know via online message if multiple BPs above 140/90
- RTC 1 mo

[ READ NOTE ]

510 — HISTORY

ENCOUNTERS    2016    May (PCP)   Jun   Jul   Aug (H)   Sep (PCP)   Oct (PCP)   Nov   Dec (PCP)   2017 Jan (PCP)   Feb (TODAY)

520 — OUTCOME

530 — SUPPORTING MEASUREMENTS

540 — LIFESTYLE

550 — ANCILLARY MEASUREMENTS

570 — PATIENT SUMMARY: GEORGE IS A 52 YEAR OLD MALE WITH HYPERTENSION, DIABETES, AND POST MI CURRENTLY TAKING LOSARTAN 50MG AND ATENOLOL 50 MG, AND HAS A SULFA ALLERGY.

580

| MEDICAL CONDITION (DISEASE) | RISK LEVEL | REASON |
|---|---|---|
| INSOMNIA | VERY HIGH | PATIENT'S EMR PROFILE CONTAINS MULTIPLE CLINICAL NOTES THAT INDICATE SLEEP DISORDER |
| NON-ALCOHOLIC FATTY LIVER DISEASE | HIGH | LAST VISIT PATIENT HAD A TRIGLYCERIDE OF 370 MG/DL. |
| CORONARY ARTERY HEART DISEASE | MODERATE | ALTHOUGH THE PATIENT QUIT SMOKING, SHE HAS A FAMILY HISTORY OF CARIDOVASCULAR COMPLICATIONS. |
| ... | ... | ... |

595 — (REASON column)
590 — (INSOMNIA row)

*FIG. 5B*

VERIFYING MEDICAL CONDITIONS OF PATIENTS IN ELECTRONIC MEDICAL RECORDS

BACKGROUND

The present application relates generally to an improved data processing apparatus and method and more specifically to mechanisms for verifying medical conditions of patients in electronic medical records.

An electronic health record (EHR) or electronic medical record (EMR) is the systematized collection of patient and population electronically-stored health information in a digital format. These records can be shared across different health care settings. Records are shared through network-connected, enterprise-wide information systems or other information networks and exchanges. EMRs may include a range of data, including demographics, medical history, medication and allergies, immunization status, laboratory test results, radiology images, radiology reports, clinical narrative notes, discharge summaries, ECHO and EKG reports, vital signs, personal statistics like age and weight, and billing information.

EMR systems are designed to store data accurately and to capture the state of a patient across time. EMR systems eliminate the need to track down a patient's previous paper medical records and assists in ensuring data is accurate and legible. EMR systems can reduce risk of data replication as there is only one modifiable file, which means the file is more likely up to date, and decreases risk of lost paperwork. Due to the digital information being searchable and in a single file, EMRs are more effective when extracting medical data for the examination of possible trends and long-term changes in a patient. Population-based studies of medical records may also be facilitated by the widespread adoption of EMRs.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided, in a data processing system comprising at least one processor and at least one memory, the at least one memory comprising instructions executed by the at least one processor to cause the at least one processor to implement a medical condition verification system. The method comprises receiving, by the medical condition verification system, patient electronic medical record (EMR) data, and parsing, by the medical condition verification system, the patient EMR data to identify an instance of a medical code or medical condition indicator present in the patient EMR data. The method further comprises performing, by the medical condition verification system, cognitive analysis of the patient EMR data to identify evidential data supportive of the instance referencing an associated medical condition. Moreover, the method comprises generating, by the medical condition verification system, a measure of risk of the patient having the medical condition based on the identified evidential data and based on a machine learned relationship of medical factors in patient EMR data relevant to generating the measure of risk for the associated medical condition. In addition, the method comprises generating, by the medical condition verification system, an output representing the measure of risk of the patient having the associated medical condition.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 5A is an example diagram of a patient EMR GUI in accordance with one illustrative embodiment;

FIG. 5B is an example diagram of the "Diseases at Risk" sub-GUI which may be output to the user in response to the user selecting the "Diseases at Risk" GUI element in FIG. 5A in accordance with one illustrative embodiment.

DETAILED DESCRIPTION

Figure 1:
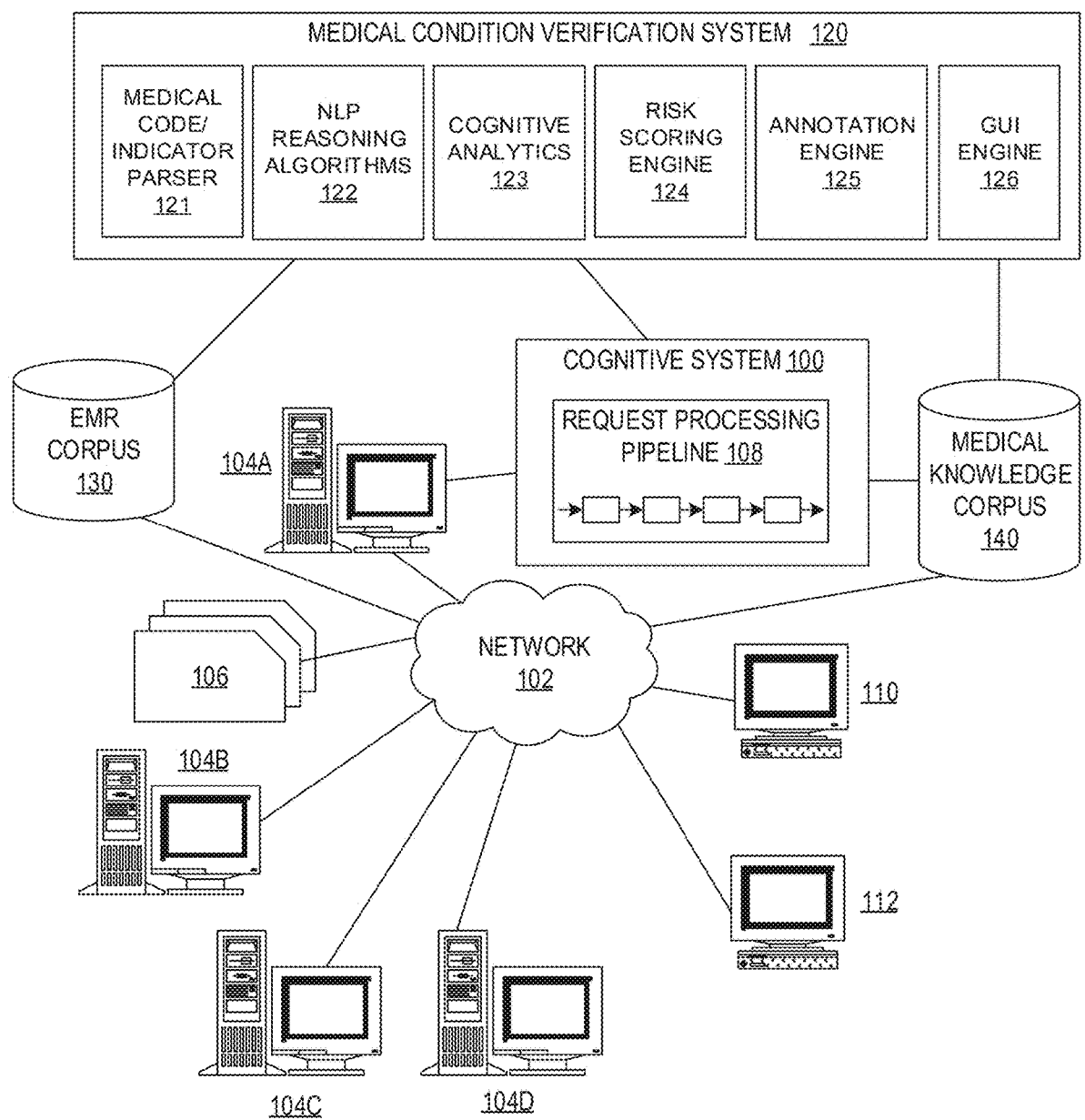
FIG. 1 depicts a schematic diagram of one illustrative embodiment of a cognitive healthcare system in a computer network.

As noted above, electronic medical record (EMR) systems provide significant advantages for tracking patient information across time, as well as potentially across multiple health product and health service providers. The EMR data maintained by such EMR systems may be used by cognitive systems, such as cognitive analytics systems, to evaluate patients based on their EMR data and provide insights into the health, medical conditions, and current and potentially useful treatments for the patients. For example, medical codes, natural language content in medical notations, and other indicators of medical conditions in patient EMR data may be used as input to a cognitive system which performs a cognitive operation to evaluate the patient to provide decision support services to medical personnel. In order for the cognitive operations of such cognitive systems to be accurate, such cognitive systems must be able to rely on the unambiguous representation of the patient's health condition specified in the patient EMR data. However, it has been recognized that often times medical codes, medical notations, and the like, may be ambiguous with regard to the actual medical condition of the patient. Such ambiguities may negatively impact the effectiveness of cognitive systems or decision support systems in generating accurate results or responses to requests.

For example, an EMR for a patient may include a code for "cancer" which may be interpreted by a cognitive system as meaning that the patient was diagnosed with cancer. However, in actuality, the patient may have merely had a biopsy to check for cancer rather than actually being diagnosed by the medical professional to actually have cancer. Due to the limitations of the medical coding systems employed, the same medical code for a medical condition may need to be utilized to code related concepts, but which are not specifically indicating that the medical condition is present. Moreover, as such medical codes are typically entered by human beings, the possibility of error in the entry of such medical codes is also present, which may lead to a cognitive system determining that a patient has a medical condition that the patient does not in fact have. Thus, because of the limitations of current medical coding systems, potential human error, and potential ambiguity in clinical notes present in an EMR, it is important to be able to distinguish between potential meanings of content in patient EMRs.

The illustrative embodiments provide mechanisms for learning the characteristics that are indicative of a medical condition actually being present in a patient, and uses these characteristics to verify indicators of medical conditions in a patient EMR, e.g., verifies medical codes or other indicators that are present in the patient EMR as being intended to represent that the patient has the corresponding medical condition rather than being associated with a related concept. That is, the invention differentiates between instances of medical codes or other medical condition indicators that actually represent the medical condition being present in the patient, and instances that are directed to related concepts, such as medical tests, laboratory results, or procedures that are related to the medical condition. Thus, ambiguities in indicators of medical conditions in the patient EMR are disambiguated based on learned characteristics indicative of actual medical conditions rather than related concepts to the actual medical condition being present for which similar medical condition indicators are utilized.

In one illustrative embodiment, the present invention provides mechanisms for identifying, from a pool of patients, which patients actually have a particular medical condition, e.g., a particular type of cancer, and which do not have the medical condition, even if the patient's EMRs contain indicators that may be interpreted as indicating that the patient has the medical condition. The mechanisms of the illustrative embodiments look at a variety of factors learned as being indicative of a medical condition to verify the indicator, e.g., medical code or other clinical note content that indicates a medical condition, to thereby verify that the patient actually does have the indicated medical condition and the medical code/content is not referencing a related concept instead. For example, the mechanism of the illustrative embodiments may determine that a patient actually does have a particular type of cancer rather than merely having a medical code in their EMR referring to a procedure related to cancer or a lab result or test related to cancer.

For example, from a large set of patient EMRs, a pool of patients may be generated that have indicators, e.g., medical codes, indicative of a particular medical condition, e.g., particular type of cancer patients, type 2 diabetes patients, insomnia patients, etc. The mechanisms of the illustrative embodiments learn, from natural language processing of guidelines documents, medical publications, information provided by subject matter experts (SMEs), e.g., clinician expertise, and the like, the patient characteristics that are supportive and/or not supportive of the hypothesis that the patient has the medical condition indicated by the medical code or other indicator of the medical condition. For example, through an ingestion of such electronic documents, various factors may be identified that are relevant to a particular medical condition, e.g., particular medical codes, patient demographics, comorbidities, medications, related medical concepts, and natural language terms/phrases associated with the medical condition or related medical concepts may be learned through a natural language processing and ingestion of the medical knowledge from these electronic documents.

Moreover, in addition to using clinician expertise, or supervised learning approaches, additional computational techniques could be used to identify patient factors for evaluating medical codes or medical condition indicators. For instance, unsupervised methods, such as Latent Dirichlet Allocation (LDA), as described in Blei et al., "Latent Dirichlet Allocation," JMLR, 3(5):993-1022, 2003, or the mechanisms described in Griffiths et al., "Finding Scientific Topics," PNAS, volume 101, pages 5228-35, 2004, may be utilized. Furthermore, human-in-the-loop methods, such as Text Nailing as described in Kartoun, "Text Nailing: An Efficient Human-in-the-Loop Text Processing Method," ACM Interactions 2017; 24(6):44-9, 2017, may be used to identify a broad range of clinical descriptors that may be applicable to evaluating the presence of medical conditions associated with medical codes or medical condition indicators.

LDA mechanisms are efficient in enhancing prediction performance in intervention outcomes, see Suresh et al., "Clinical Intervention Prediction and Understanding Using Deep Networks," Proceedings of the 2nd Machine Learning for Healthcare Conference, 2017. LDA mechanisms are also efficient in understanding physician prescription patterns within the context of insomnia, see Beam et al., "Predictive Modeling of Physician-Patient Dynamics that Influence Sleep Medication Prescriptions and Clinical Decision-Making," Sci. Rep. 2017:9; 7:42282. Text Nailing has been tested in multiple scenarios, including the extraction of smoking status, family history of coronary artery disease (see Corey et al., Using an Electronic Medical Records Database to Identify Nontraditional Cardiovascular Risk Factors in Nonalcoholic Fatty Liver Disease," Am J Gastroenterol 2016; 111(5):671-6)), classifying patients with sleep disorders (Beam et al. 2017 referenced above), and improving the accuracy of the Framingham risk score for patients with nonalcoholic fatty liver disease, see Simon et al., "MELD-Na Score Predicts Incident Major Cardiovascular Events in Patients with Nonalcoholic Fatty Liver Disease," Hepatol Commun 2017; 1(5):429-38.

Various structured and unstructured covariates may be learned to be relevant to the evaluation of the presence of a particular medical condition. Moreover, the particular combination of structured and unstructured covariates applicable to a particular medical condition may differ substantially from the combination of covariates used to evaluate other medical conditions. As an example, structured covariates for insomnia may include certain International Classification of Diseases (ICD) codes (e.g., ICD-9, ICD-10, etc.) or Diagnosis Related Group (DRG) codes for insomnia, a sleep study or additional procedures represented, for instance, by Current Procedural Terminology (CPT) codes, socioeconomic characteristics including age, gender, and ethnicity, particular comorbidities including diabetes, anxiety/depression, renal failure, hypertension, CHF, etc., and medications such as Trazodone, Ambien, and the like. Additional procedures may include a surgery, a blood transfusion, deep brain stimulation, etc. It is noted that our invention is not limited to a specific billing method (such as ICDs and CPTs) and it could be applicable in international healthcare systems that use different billing/clinical documentation methods. Unstructured covariates may include various learned terms or phrases associated with particular medical concepts related to the medical condition, e.g., for insomnia terms/phrases associated with sleep disorder, alcohol use, smoking status, psychiatric disorders, and body mass index (BMI) may be relevant to the evaluation of the actual presence of insomnia in the patient or not. An evaluation of these characteristics with regard to each of the patients in the pool of patients is performed to determine a likelihood that the patient actually has the medical condition indicated or the medical coding or other indicator is likely associated with a related concept rather than the actual medical condition itself.

During a training phase of development of the medical condition verification system of the illustrative embodiments, the medical condition verification system may evaluate patient EMRs to determine, for each medical condition for which the mechanisms are being trained, a risk score, e.g., an instance probability, for the medical condition, e.g., disease, based on an evaluation of the structured and unstructured covariates established for the particular medical condition. A formula may be implemented to calculate the risk score for the medical condition, e.g., disease, where the formula comprises one or more characteristics, such as comorbidities, medications, laboratory measurements, and mentions in clinical narrative notes. A combination of structured and unstructured covariates may be used to calculate the risk score of the patient using such a function.

For example, for an insomnia medical condition, the probability of insomnia, and thus the risk score for insomnia, may be calculated using the following formula in one illustrative embodiment, considering patient's history (either restricted by a time range, e.g., 12 months, or unrestricted):

$$I = X + a^*[\#Insomnia] + b^*[\#Anxiety\ and\ Depression] + c^*[\#Joint\ Disorder] + d^*[\#EMR\ Facts] + e^*[\#Sleep\ Medications] + f^*[\#Sleep\ Disorder] + g^*[\#Psychiatric\ Disorder] \quad (1)$$

$$P(Insomnia) = \exp(I)/(1+\exp(I)) \quad (2)$$

where, in equation (1) above, X is a constant, "a" through "g" are coefficients whose values are learned through machine learning and training of the medical condition verification system, and the factors in brackets indicate a number of instances of factors corresponding to the particular factor type, e.g., number of occurrences of the medical code for insomnia in the patient's EMR, number of instances of mentions of anxiety and depression concepts in the patient EMR, number of instances of mentions of joint disorder in the patient EMR, number of sleep medications the patient is on, number of sleep disorders mentioned in the patient's EMR, number of psychiatric disorders mentioned in the EMR, etc. that are associated with insomnia. That is, for each of these types of factors, for the particular medical condition, certain medical codes, indicators, non-negated terms/phrases extracted from clinical narrative notes corresponding to particular ones of these types of factors that are relevant to the presence, or non-presences, of the medical condition (insomnia) may be provided and in determining the risk score for the medical condition, those particular factors are used to generate the values for entry into the [# . . . ] elements of equation (1) above. Thereafter, the probability P of the medical condition is calculated using equation (2) to thereby generate the risk score for the medical condition being present in the patient.

The risk score may be compared to one or more predetermined threshold values to determine a prediction of whether the patient is actually confidently suspected to have the medical condition or not, i.e. the probability is sufficiently high (equal to or above the threshold) to indicate that the medical condition is likely present, or is sufficient low (equal to or below another threshold) to indicate that the medical condition is not likely present. In some cases, there may be a third band of probabilities where it cannot be determined whether or not the patient has the medical condition or not, e.g., between the first threshold and the second threshold, in which case a corresponding probability and indication of an indeterminate outcome may be generated by the medical condition verification system.

It should be noted that probability is only an example to assess indications of medical conditions. Additional measures may include, for instance, standard numerical ranges, such as 1: low risk to 10: high risk. Moreover, a variety of computational techniques, unrestricted to logistic regression, may be used to calculate that risk, which could be a probability, a number, a phrase, such as "low risk," "intermediate risk," "high risk," for example, etc.

The risk score may be compared to a ground truth for the particular patient to determine if the medical condition verification system has correctly or incorrectly identified the particular patient as having the particular medical condition. In response to an error being present, e.g., the medical condition verification mechanism determining that wrong result, a computational process (such as machine learning algorithm) is employed to adjust the operational parameters, e.g., weights associated with different structured/unstructured covariates, of the medical condition verification system to reduce the error and increase the accuracy in the risk score calculations. Thus, through the machine learning and training of the medical condition verification system using a training pool of patients, some of which may have the medical condition, and some of which may not have the medical condition, the medical condition verification system is trained to identify other structured and unstructured characteristics in a patient's EMR that may be used to verify, or even invalidate, the presence of a medical condition with regard to the patient as indicated by a medical code or other indicator in the patient EMR. Furthermore, through using machine learning and training, a human expert (such as a clinician) is involved to label patient EMRs as confidently having a medical condition, or to rule it out. Such a process may be referred to as "performing clinical chart review."

During runtime operation, after the training of the medical condition verification system has been completed, the medical condition verification system may evaluate medical condition indicators, e.g., medical codes or other medical condition indicators, in a patient EMR of an actual patient being treated by a physician or other medical personnel, either prior, after, or commensurate with an encounter with the patient. Based on the results of the evaluation, the medical condition verification system may add annotations to the patient EMR to indicate whether the particular medical codes or other medical condition indicators (assumed hereafter to be medical codes for purposes of ease of explanation) are in fact valid indicators of the medical condition or are associated with a related concept to the medical condition and not in fact indicative of the medical condition itself being present in the patient. That is, each instance of a medical code or medical condition indicator may be separately evaluated and an annotation or metadata specifying the instance of the medical code or medical condition indicator and the results of the medical condition verification system operations may be added to the patient EMR to thereby generate a disambiguated patient EMR.

Moreover, such operations may be performed responsive to a new medical code or medical condition indicator being added to an existing patient EMR such that only the new medical code or medical condition indicator is evaluated in the manner described previously. In this way, the patient EMR may be dynamically updated with annotations specifying the veracity of the medical codes or medical condition indicators with regard to their specifying existence of the corresponding medical condition, e.g., disease.

Alternatively, or in addition to the annotation of the patient EMRs, the medical condition verification system may generate a user interface, or augment another user interface, for viewing the patient EMR, such that the user interface identifies the validity/invalidity of the particular medical condition being present in the patient. For example, the mechanisms of the illustrative embodiments may generate a user interface that may be presented to medical personnel, where the user interface may include a listing of medical conditions potentially associated with the patient along with corresponding risk scores and an indication of whether or not the patient is at a high risk or not of having the medical condition, e.g., the patient's risk score for the medical condition equals or exceeds a predefined threshold. For example, the graphical user interface may have a selectable graphical user interface element, e.g., a virtual button or the like, that may be selected by a physician or other medical personnel to view the listing of medical conditions the patient may be suspected to have, or at an increased risk to have, and comments indicating how the risk score was determined, e.g., what covariates were evaluated, which covariates were most influential in the determination of the risk score, etc. This information may be presented in a structured manner, such as in a table or other structured representation of a graphical user interface, or in a natural language note or portion of text, or a combination of structured and unstructured formats.

Thus, the physician or other medical personnel are informed via the user interface of which medical conditions the patient is likely to have despite medical codes or other medical condition indicators that may be directed to related concepts rather than actual presence of the corresponding medical condition. The medical condition verification system verifies whether such medical codes or medical condition indicators are identifying the presence of the medical condition or not based on the covariates present in the patient EMR and determines the risk scores appropriately to present to the physical or medical personnel the actual risk of the patient having a medical condition. In this way, the illustrative embodiments differentiate medical codes or indicators that actually are specifying the medical condition to be present from those that are associated with related concepts rather than actually specifying the medical condition to be present.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides mechanisms for verifying the existence or non-existence of a medical condition corresponding to a medical code or other medical condition indicator present in a patient's electronic medical record (EMR) or electronic health record (EHR). The illustrative embodiments implement a method, computer program product, and/or data processing system that is specifically configured with logic for implementing a medical condition verification system that operates to verify the presence or non-presence of a medical condition in a patient that is associated with a medical code or other medical condition indicator (again, generally referenced herein as a medical code for ease of explanation) based on the presence, or lack thereof, of other instances of factors in the patient's EMR providing evidential support for the existence or non-existence of the medical condition being associated with the patient. Thus, simply because a medical code is present in the patient EMR does not mean that the corresponding medical condition will be attributed to the patient unless there is other evidence present in the patient's EMR indicating that the medical condition corresponding to the medical code is likely associated with the patient and thus, the medical code is specifying the medical condition and not simply a related concept.

Figure 2:
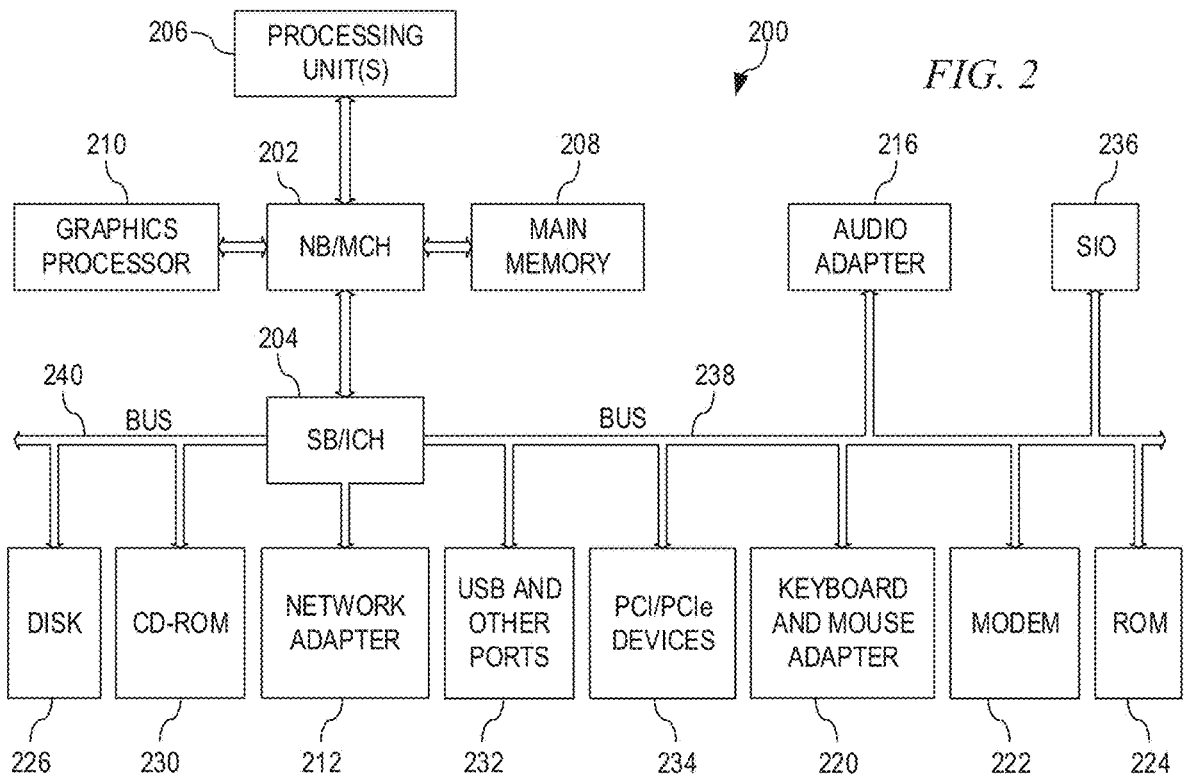
FIG. 2 is a block diagram of an example data processing system in which aspects of the illustrative embodiments are implemented.
Figure 3:
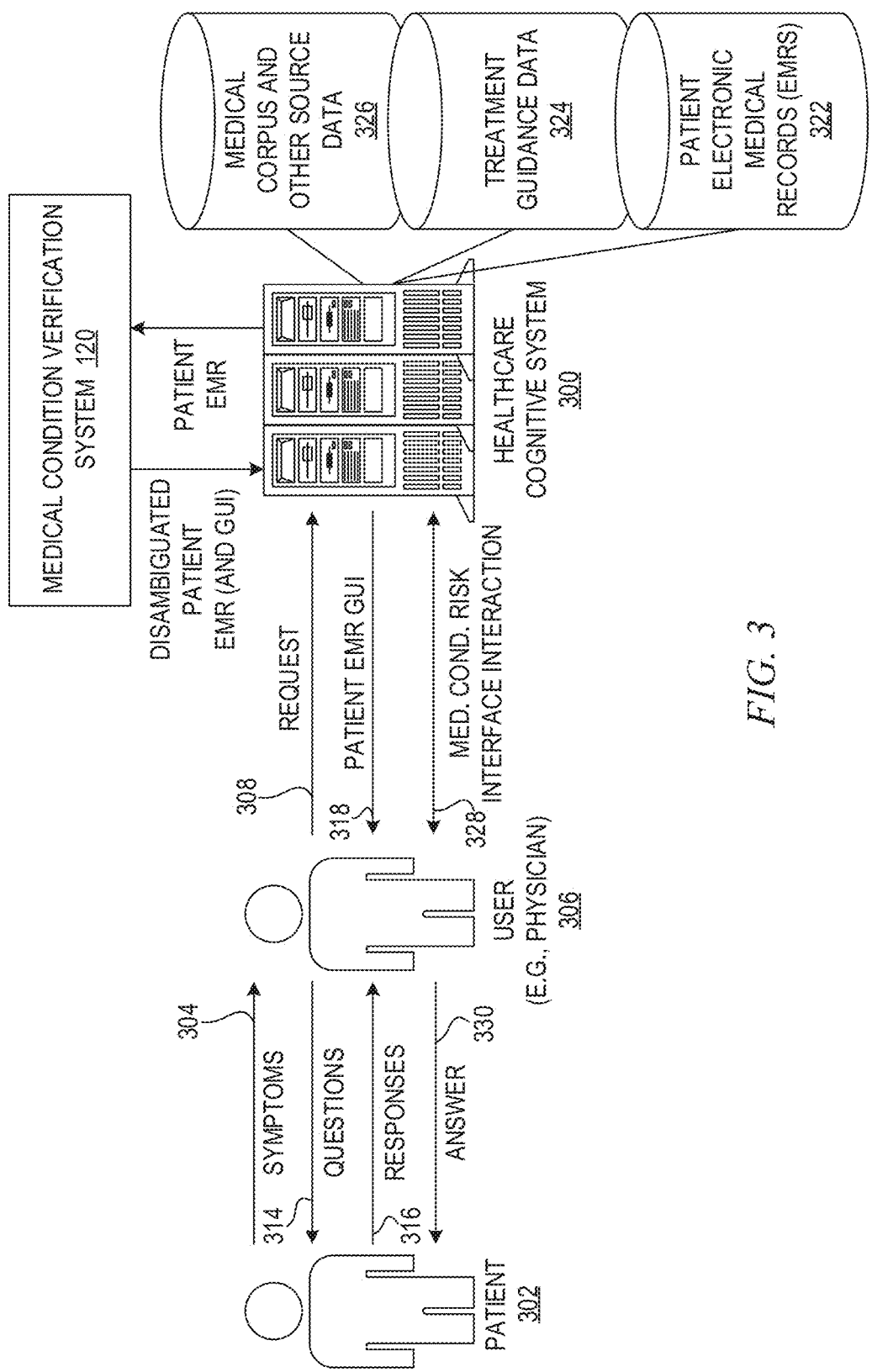
FIG. 3 is an example diagram illustrating an interaction of elements of a healthcare cognitive system in accordance with one illustrative embodiment.

The illustrative embodiments may be utilized in many different types of data processing environments. In order to provide a context for the description of the specific elements and functionality of the illustrative embodiments, FIGS. 1-3 are provided hereafter as example environments in which aspects of the illustrative embodiments may be implemented. It should be appreciated that FIGS. 1-3 are only examples and are not intended to assert or imply any limitation with regard to the environments in which aspects or embodiments of the present invention may be implemented. Many modifications to the depicted environments may be made without departing from the spirit and scope of the present invention.

FIGS. 1-3 are directed to describing an example cognitive system for healthcare applications (also referred to herein as a "healthcare cognitive system") which implements a request processing pipeline, request processing methodology, and request processing computer program product with which the mechanisms of the illustrative embodiments are implemented. These requests may be provided as structure or unstructured request messages, natural language questions, or any other suitable format for requesting an operation to be performed by the healthcare cognitive system. As described in more detail hereafter, the particular healthcare application that is implemented in the cognitive system of the present invention is a healthcare application for identifying medical conditions and their corresponding probabilities of being associated with the patient based on the content of the patient's EMR and characteristics of the patient. In particular, the healthcare application presents a graphical user interface that, at least in part, provides a graphical user interface element through which a user, such as a physician or other medical personnel, may request that the diseases that the patient is at risk of having are listed along with the corresponding risk and supporting evidence for that determined level of risk, either in a structured, unstructured, or combination representation.

It should be appreciated that the healthcare cognitive system, while shown as having a single request processing pipeline in the examples hereafter, may in fact have multiple request processing pipelines. Each request processing pipeline may be separately trained and/or configured to process patient EMRs with regard to different domains. For example, in some cases, a first request processing pipeline may be trained to operate on input requests directed to a first medical condition domain, e.g., various types of blood diseases, while another request processing pipeline may be trained to operate to evaluate patient EMRs with regard to another medical condition domain, e.g., various types of cancers, and yet another request processing pipeline may be trained to operate to evaluate patient EMRs with regard to a third domain, e.g., sleep disorders. In other cases, for example, the request processing pipelines may be configured to provide different types of cognitive functions or support different types of healthcare applications, such as one request processing pipeline being used for patient diagnosis, another request processing pipeline being configured for medical treatment recommendation, another request processing pipeline being configured for patient monitoring, etc.

Moreover, each request processing pipeline may have their own associated corpus or corpora that they ingest and operate on, e.g., one corpus for blood disease domain documents and another corpus for cancer diagnostics domain related documents in the above examples. In some cases, the request processing pipelines may each operate on the same domain of input requests but may have different configurations, e.g., different annotators or differently trained annotators, different analytics, different probability calculation functions utilizing different combinations of factors for different medical conditions and correspondingly trained weights or coefficients for the various factors, etc. such that different analysis and potential responses are generated. The healthcare cognitive system may provide additional logic for routing input questions to the appropriate request processing pipelines, such as based on a determined domain of the input request, particular medical codes or medical condition indicators specified in the patient's EMR, etc. and may further comprise logic for combining and evaluating final results generated by the processing performed by multiple request processing pipelines. Moreover, the healthcare cognitive system may comprise other control and interaction logic that facilitates the utilization of multiple request processing pipelines.

As will be discussed in greater detail hereafter, the illustrative embodiments may be integrated in, augment, and extend the functionality of these request processing pipeline mechanisms of a healthcare cognitive system with regard to verifying the medical codes or other medical condition indicators based on other evidence present in the patient EMR and ingested knowledge from knowledge sources, such as electronic documents in an electronic corpus or corpora.

A variety of scientific publications analyze the correctness of structured variables (such as ICD diagnosis codes) within the context of specific diseases. Such publications often propose levels of confidence of disease codes. For instance, Liao K P et al., "Electronic Medical Records for Discovery Research in Rheumatoid Arthritis," Arthritis Care Res (Hoboken)2010; 62:1120-7 proposes that a combination of narrative and codified data can classify rheumatoid arthritis (RA) subjects with a positive predictive value (PPV) of 94%, while codified data alone with PPV of 88%. Additional examples include Crohn's and ulcerative colitis diseases as in Ananthakrishnan et al., "Improving Case Definition of Crohn's Disease and Ulcerative Colitis in Electronic Medical Records Using Natural Language Processing: A Novel Informatics Approach," Inflamm Bowel Dis 2013; 19:1411-20. While illustrative embodiments of the present invention may rely primarily on EMR data, the illustrative embodiments may also integrate disease-specific confidence indicators extracted from publicly available scientific papers. The confidence indicators, such as PPV values for using ICD codes, mentions in notes, etc., per disease, extracted from the scientific papers, may then be integrated with EMR data.

The mechanisms of the illustrative embodiments allow for annotation of patient EMRs and/or generation of a graphical user interface output that clarifies, or disambiguates, the medical codes or other indicators of medical conditions in the patients' EMRs with regard to whether or not they actually are referencing the patient having the corresponding medical condition or whether they are referencing a related concept without specifically identifying the patient as having the medical condition. Moreover, in some illustrative embodiments, the disambiguated patient EMRs may be used by healthcare cognitive systems to perform healthcare cognitive operations, such as diagnosis, patient treatment recommendation, patient monitoring, or any other decision support based cognitive system operation that supports decision making by a human medical professional, or other medical personnel, when evaluating and/or treating a patient.

Thus, as the mechanisms of the illustrative embodiments may be integrated in or operate in conjunction with a cognitive system, it is important to have an understanding of how cognitive systems and request processing pipelines are implemented before describing how the mechanisms of the illustrative embodiments are integrated in and augment such cognitive systems and request processing pipelines. It should be appreciated that the mechanisms described in FIGS. 1-3 are only examples and are not intended to state or imply any limitation with regard to the type of cognitive system mechanisms with which the illustrative embodiments are implemented. Many modifications to the example cognitive system shown in FIGS. 1-3 may be implemented in various embodiments of the present invention without departing from the spirit and scope of the present invention.

The cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

IBM Watson™ is an example of one such cognitive system which can process human readable language and identify inferences between text passages with human-like high accuracy at speeds far faster than human beings and on a larger scale. In general, such cognitive systems are able to perform the following functions:

- Navigate the complexities of human language and understanding
- Ingest and process vast amounts of structured and unstructured data
- Generate and evaluate hypothesis
- Weigh and evaluate responses that are based only on relevant evidence
- Provide situation-specific advice, insights, and guidance
- Improve knowledge and learn with each iteration and interaction through machine learning processes
- Enable decision making at the point of impact (contextual guidance)
- Scale in proportion to the task
- Extend and magnify human expertise and cognition
- Identify resonating, human-like attributes and traits from natural language
- Deduce various language specific or agnostic attributes from natural language
- High degree of relevant recollection from data points (images, text, voice) (memorization and recall)
- Predict and sense with situational awareness that mimic human cognition based on experiences
- Answer questions based on natural language and specific evidence In the context of the illustrative embodiments, in addition to these general functions performed by cognitive systems, the healthcare cognitive system with which the illustrative embodiments may operate may perform various other types of cognitive operations for analyzing patient EMR data and generating insights into the health of the patient and/or treatment of the patient. For example, the healthcare cognitive system may operate to perform one or more cognitive analytics on the patient EMR data and/or other data obtained from various other data sources regarding the patient and/or patient health to generate insights, i.e. information about the patient extracted from cognitive analysis of raw data to identify correlations, patterns, trends, or other indicators not explicit in the raw data itself. For example, a request processing pipeline of a healthcare cognitive system may receive patient information, either from the patient EMR data, other sources of patient information, or both, and perform a set of one or more cognitive analytics on the patient information to generate insight information, such as identifying and extracting non-negated clinical descriptors as, for example, shown in FIG. 4(A)-(C). which itself may be the basis of further cognitive operations and/or may be used to generate graphical user interface outputs for providing the insight information to medical personnel to assist them in evaluating and treating the patient.

In some illustrative embodiments, the request processing pipeline of the cognitive system receives an input request, which may be automatically generated by a computing system in response to other events, or may be generated by a user input specifically requesting a cognitive operation to be performed, parses the request to extract the major features of the request, uses the extracted features to formulate queries, and then applies those queries to a corresponding electronic corpus or corpora of data. In the context of the illustrative embodiments, the electronic corpus or corpora may include patient EMR data, patient information from other source computing systems, medical resource data, guidelines documents, and other sources of medical knowledge. Based on the application of the queries to the electronic corpus or corpora of data, the request processing pipeline generates a set of candidate responses to the input request, by looking across the electronic corpus or corpora of data for portions of the electronic corpus or corpora of data that have some potential for containing a valuable response to the input request. The request processing pipeline then performs deep analysis on the input request and the portions of the electronic corpus or corpora of data found during the application of the queries using a variety of reasoning algorithms and/or cognitive analytics. There may be hundreds or even thousands of reasoning algorithms and/or cognitive analytics applied, each of which performs different analysis, e.g., comparisons, natural language analysis, lexical analysis, pattern or trend analysis, various correlations of related concepts, or the like, and generates a score for each of the candidate responses. For example, some reasoning algorithms may look at the matching of terms and synonyms within the language of the input question and the found portions of the electronic corpus or corpora of data. Other reasoning algorithms may look at temporal or spatial features in the language, while others may evaluate the source of the portion of the electronic corpus or corpora of data and evaluate its veracity.

The scores obtained from the various reasoning algorithms and/or cognitive analytics indicate the extent to which the potential response is inferred by the input request based on the specific area of focus of that reasoning algorithm and/or cognitive analytic. Each resulting score is then weighted against a statistical model. The statistical model captures how well the reasoning algorithm and/or cognitive analytic performed at establishing the inference between two similar passages for a particular domain during the training period of the request processing pipeline. The statistical model is used to summarize a level of confidence that the request processing pipeline has regarding the evidence that the potential response is inferred by the input request. This process is repeated for each of the candidate responses until the request processing pipeline identifies candidate responses that surface as being significantly stronger than others and thus, generates a final response, or ranked set of responses, for the input request.

In the context of the illustrative embodiments of the present invention, the request processing pipeline may evaluate an automatically generated, implied, or user specified request to disambiguation medical codes or medical condition indicators in a specific patient EMR. Responsive to such a request, the request processing pipeline may parse the patient EMR data to identify medical codes or medical condition indicators that are to be disambiguated. Each medical code, or medical condition indicator, may then be evaluated by applying a plurality of reasoning algorithms and/or cognitive analytics to evaluate various other information present in the EMR data and/or other sources of patient information to determine a score for each medical code or medical condition indicator indicative of the probability that the medical code or indicator indicates an actual medical condition or not. Based on the scores, and one or more pre-established thresholds, a set of instances of the medical codes or indicators satisfying a criteria of a threshold indicative of an actual medical condition being identified, may be annotated or otherwise identified as indicating an actual medical condition of the patient which may be included in a medical condition listing for the patient, and which may be used to generate a natural language summary of the patient's medical conditions. For other medical code or indicator instances that are equal to or less than another threshold (e.g., minimum threshold) indicative of the medical code or indicator being associated with a related concept and not referencing an actual medical condition, these instances may be annotated accordingly and may be eliminated from a listing of medical conditions associated with the patient or listings of potential risks for medical conditions. Other instances of medical codes or indicators that have sufficient supportive evidence to raise their score above the minimum threshold, but not equal to or above a threshold to indicate that the patient actual has the corresponding medical condition, may be classified as medical conditions for which the patient has some measure of risk indicated in their EMR data. These medical codes or indicators may be used to generate a listing of medical conditions for which the patient is at risk with corresponding risk levels and evidential support reasoning as obtained from the portions of the patient EMR data and/or other patient information sources, or even the guidelines and other electronic corpus documentation.

FIG. 1 depicts a schematic diagram of one illustrative embodiment of a cognitive system 100 implementing a request processing pipeline 108 in a computer network 102. The cognitive system 100 is implemented on one or more computing devices 104A-D (comprising one or more processors and one or more memories, and potentially any other computing device elements generally known in the art including buses, storage devices, communication interfaces, and the like) connected to the computer network 102. For purposes of illustration only, FIG. 1 depicts the cognitive system 100 being implemented on computing device 104A only, but as noted above the cognitive system 100 may be distributed across multiple computing devices, such as a plurality of computing devices 104A-D. The network 102 includes multiple computing devices 104A-D, which may operate as server computing devices, and 110-112 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 100 and network 102 enables cognitive request processing functionality for one or more cognitive system users via their respective computing devices 110-112. In other embodiments, the cognitive system 100 and network 102 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 100 may be used with components, systems, sub-systems, and/or devices other than those that are depicted herein.

The cognitive system 100 is configured to implement a request processing pipeline 108 that receive inputs from various sources. In some illustrative embodiments, the requests may be posed in the form of a natural language question, natural language request for information, natural language request for the performance of a cognitive operation, or the like, or may be posed in the form of a request to perform a cognitive operation on a particular portion of data, e.g., a specified patient EMR, set of patient EMRs, or the like, e.g., "perform disambiguation on John Smith's EMR" or an automated instruction to perform such an operation. For example, the cognitive system 100 receives input from the network 102, a corpus or corpora of electronic documents 106, cognitive system users, and/or other data and other possible sources of input. In one embodiment, some or all of the inputs to the cognitive system 100 are routed through the network 102. The various computing devices 104A-D on the network 102 include access points for content creators and cognitive system users. Some of the computing devices 104A-D include devices for a database storing the corpus or corpora of data 106 (which is shown as a separate entity in FIG. 1 for illustrative purposes only). Portions of the corpus or corpora of data 106 may also be provided on one or more other network attached storage devices, in one or more databases, or other computing devices not explicitly shown in FIG. 1. The network 102 includes local network connections and remote connections in various embodiments, such that the cognitive system 100 may operate in environments of any size, including local and global, e.g., the Internet.

In one embodiment, the content creator creates content in a document of the corpus or corpora of data 106 for use as part of a corpus of data with the cognitive system 100. The document includes any file, text, article, or source of data for use in the cognitive system 100. Cognitive system users access the cognitive system 100 via a network connection or an Internet connection to the network 102, and input requests to the cognitive system 100 that are processed based on the content in the corpus or corpora of data 106. The cognitive system 100 parses and interprets the request via a pipeline 108, and provides a response to the cognitive system user, e.g., cognitive system user 110, containing one or more responses to the request, results of processing the request, or the like. In some embodiments, the cognitive system 100 provides a response to users in a ranked list of candidate responses while in other illustrative embodiments, the cognitive system 100 provides a single final response or a combination of a final response and ranked listing of other candidate responses, e.g., a final response in terms of the medical condition summary of the patient specifying medical conditions determined to actually be present with the patient, and a ranked listing of other candidate medical conditions which the patient is at risk of having based on the cognitive processing of the patient's EMR and other patient information and knowledge source documentation in a corpus or corpora.

The cognitive system 100 implements the pipeline 108 which comprises a plurality of stages for processing an input request based on information obtained from the corpus or corpora of data 106 and/or medical knowledge corpus 140. The pipeline 108 generates responses for the input request based on the processing of the input request and the corpus or corpora of data 106. The various stages of the pipeline 108 may perform different types of analysis on the input request and/or information retrieved from patient EMRs, other sources of patient information, and/or electronic documentation from medical knowledge resource sources of one or more corpora. For example, an initial stage of the pipeline 108 may parse the request to extract features of the request. Another stage of the pipeline may process the extracted features of the request to generate queries that may be applied to databases or other storage systems storing patient EMR data, patient information, and/or electronic documents of one or more corpora. In other stages of the pipeline 108, the patient EMR data and/or patient information may be parsed to identify instances of medical codes and/or medical condition indicators which may need to be disambiguated. In still further stages of the pipeline 108, specific reasoning algorithms and/or cognitive analytics may be applied to the retrieved patient EMR data, patient information from other sources, and/or electronic documents so as to generate individual factor scores which may be combined in a further stage, such as using equations (1) and (2) above, to generate probability predictions or "risk scores" for medical conditions indicated by the one or more instances of medical codes and/or medical condition indicators in the patient EMR data and/or patient information.

In some illustrative embodiments, the cognitive system 100 may be the IBM Watson™ cognitive system available from International Business Machines Corporation of Armonk, N.Y., which is augmented and/or specifically configured with the mechanisms of the illustrative embodiments described herein. As outlined previously, a pipeline of the IBM Watson™ cognitive system receives an input request which it then parses to extract the major features of the request, which in turn are then used to formulate queries that are applied to the corpus or corpora of data 106, 140. Based on the application of the queries to the corpus or corpora of data 106, 140, a set of hypotheses, or candidate responses (e.g., medical conditions in the present illustrative embodiments) to the input request, are generated by looking across the corpus or corpora of data 106, 140 for portions of the corpus or corpora of data 106, 140 (hereafter referred to simply as the corpus 106, 140) that have some potential for containing a valuable response to the input request. The pipeline 108 of the IBM Watson™ cognitive system then performs deep analysis on the input request and the portions of the corpus 106, 140 found during the application of the queries using a variety of reasoning algorithms. In accordance with the illustrative embodiments such queries and deep analysis may also be applied to patient EMR data for one or more specified patients, obtained from the EMR corpus 130.

The scores obtained from the various reasoning algorithms are then weighted against a statistical model that summarizes a level of confidence that the pipeline 108 of the IBM Watson™ cognitive system 100, in this example, has regarding the evidence that the potential candidate response is inferred by the input request, e.g., in the illustrative embodiments a level of confidence that a specific medical condition associated with an instance of a medical code or medical condition indicator in the patient's EMR is actually present in the patient. This process is be repeated for each of the candidate responses (e.g., medical conditions associated with medical codes or medical condition indicators in the patient's EMR data) to generate a ranked listing of candidate responses (e.g., medical conditions) which may then be presented to a user or otherwise utilized to perform other cognitive operations at least partially based on the ranked listing of candidate responses and their associated scores (e.g., risk scores). In some cases, the cognitive system 100 may return a graphical user interface to the user that submitted the input request, e.g., a user of client computing device 110, for summarizing the medical condition of the patient in response to the user selecting an option to present such information via the graphical user interface (GUI). More information about the pipeline 108 of the IBM Watson™ cognitive system 100 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

In the context of the present invention, cognitive system 100 may provide additional cognitive functionality for assisting with healthcare based operations, e.g., providing decision support services to medical personnel, at least partially based on the disambiguation of medical codes or medical condition indicators in the patient EMR data. For example, depending upon the particular implementation, the healthcare based operations may comprise patient diagnostics, medical treatment recommendation systems, personal patient care plan generation and monitoring, patient electronic medical record (EMR) evaluation for various purposes, such as for identifying patients that are suitable for a medical trial or a particular type of medical treatment, or the like. Thus, the cognitive system 100 may be a healthcare cognitive system 100 that operates in the medical or healthcare type domains and which may process requests for such healthcare operations via the request processing pipeline 108 input as either structured or unstructured requests, natural language input questions, or the like. In one illustrative embodiment, the cognitive system 100 is a patient medical condition report generation system that provides graphical user interface(s) with which a medical professional, such as a physician, may interact to obtain information about the medical conditions of the patient, the manner by which the patient has been treated including detailed histories of patient encounters, prescribed treatments, outcomes, supporting medical measurements, lifestyle information about the patient, and the like. In particular as part of this graphical user interface (GUI) mechanism, a "disease at risk" option is provided through which the medical professional may access a summary of the medical conditions the patient is believed to have and those that the patient is at risk for, including indicators of a level of risk and the supporting evidence for the evaluation of such a level of risk, based on the disambiguation of the medical codes and medical condition indicators in the patient EMR data performed by the mechanisms of the illustrative embodiments.

As shown in FIG. 1, the cognitive system 100 is further augmented, in accordance with the mechanisms of the illustrative embodiments, to include logic implemented in specialized hardware, software executed on hardware, or any combination of specialized hardware and software executed on hardware, for implementing a medical condition verification system 120. The medical condition verification system 120 for learning the characteristics that are indicative of a medical condition actually being present in a patient, and using these learned characteristics to verify indicators of medical conditions in a patient EMR as actually indicating the presence of the corresponding medical conditions, as indicating related concepts but not the actual presence of the corresponding medical condition yet giving rise to a potential risk of the corresponding medical condition being present in the patient, or as being erroneous or not reaching a minimum level of evidential support to indicate a risk of the corresponding medical condition with regard to the patient. Thus, ambiguities in indicators of medical conditions in the patient EMR data from the EMR corpus 130 for a specified patient, or group of patients, are disambiguated based on learned characteristics indicative of actual medical conditions and risks of medical conditions indicated by medical codes or medical condition indicators may be predicted and used to provide an output for decision support cognitive operations.

As shown in FIG. 1, the medical condition verification system 120 comprises a medical code/indicator parser 121, one or more natural language processing (NLP) reasoning algorithms 122, one or more cognitive analytics 123, a risk scoring engine 124, a medical condition identification and ranking engine 125, and a GUI engine 126. Other logic not explicitly shown in FIG. 1 may also be provided in the medical condition verification system 120 for controlling various operations of the medical condition verification system 120 and orchestrating the operation of the depicted elements 121-126. Any functionality or operations not specifically attributed to one of the depicted elements 121-126 may be performed by this other logic present within the medical condition verification system 120 without departing from the spirit and scope of the present invention.

Moreover, while FIG. 1 shows the medical condition verification system 120 as a separate element in FIG. 1 from the cognitive system 100 or pipeline 108, it should be appreciated that the illustrative embodiments are not limited to such. To the contrary, the medical condition verification system 120, or portions thereof, may be integrated in the cognitive system 100 and/or pipeline 108 and may work in conjunction with the cognitive system 100 and/or pipeline 108.

A request may be automatically generated, such as in response to a detected change in a patient EMR in the EMR corpus 130, in response to another computing device automatically requesting a disambiguation of a patient EMR, automatically initiating such disambiguation on a scheduled basis, or the like. The request may also be generated manually by a user, such as via a client computing device 110, such as when a physician requests to review a patient's EMR, a user requests disambiguation of one or more patient EMRs in the EMR corpus 130, or the like. In response to receiving such a request, the cognitive system 100 may invoke the operation of the medical condition verification system 120 to disambiguate or verify instances of medical codes or medical condition indicators in one or more patient EMRs present in the EMR corpus 130. For example, a physician may initiate a request via their client computing device 110 to review patient "John Smith" EMR data stored in the EMR corpus 130. The request may be received by the cognitive system 100 which invokes the medical condition verification system 120 to disambiguate and verify medical codes or medical condition indicators in John Smith's EMR data retrieved form the EMR corpus 130 by the cognitive system 100. The medical condition verification system 120 may then process the patient EMR data, other patient information retrieved from other patient information source computing systems if applicable, and guideline documents, medication resource documentation, and other medical knowledge resources from one or more corpora 106, 140, and return a disambiguated patient EMR for John Smith which may be annotated to identify which instances of medical codes/indicators are referencing the medical condition being present in the patient, which are indicative of a potential risk of a medical condition and what that risk level may be, and those that may be erroneous or not sufficiently supported by other evidence to indicate a risk of the medical condition being present within the patient. Moreover, the medical condition verification system 120 may provide a GUI output which may be itself returned to the physician or may be combined with other GUIs generated by the cognitive system 100 for presenting patient EMR data to the user (physician). For example, the GUI generated by the medical condition verification system 120 may be added as a sub-GUI that is accessible via another GUI via a user selectable element, e.g., a "Diseases at Risk" button or other selectable element in the GUI.

The medical code/indicator parser 121 may parse and process the patient EMR data for the patient to identify instances of medical codes or other medical condition indicators, e.g., names of diseases, names of medical conditions, natural language concepts associated with specific diseases or medical conditions, abbreviations representing medical conditions, or the like. From this parsing, a listing of potential medical conditions that the patient may have may be generated, eliminating any duplicates. Each of the medical conditions may then be processed via the one or more NLP reasoning algorithms 122 and/or cognitive analytics 123 to generate supportive evidence for the existence of the medical condition in the patient. The NLP reasoning algorithms 122 may analyze natural language content of the patient EMR data and other information from the various corpora 106, 140, for identifying terms/phrases within the patient EMR data and other corpora 106, 140 that are supportive of, or not supportive of, the medical condition being present in the patient. The cognitive analytics 123 may analyze various medical lab results, demographic classifications of the patient, lifestyle information about the patient, etc. and may apply medical knowledge to such patient information to identify patterns, trends, associations, and the like, that may be supportive of, or not supportive of, the medical condition being present in the patient. The results of these evaluations are considered to be evidential information associated with a medical condition. The evidential information, and source and reasoning associated with this evidential information, may be maintained in association with the medical condition, which in turn is associated with the instances of medical codes/indicators in the EMR data.

The evidential information generated by the NLP reasoning algorithms 122 and/or cognitive analytics 123 may be provided to the risk scoring engine 124 which may generate a risk score, or probability prediction, indicating a probability that the patient has the corresponding medical condition or is at risk of having the corresponding medical condition. For example, for the particular medical condition, a listing of factors for evaluating the probability of the medical condition being present retrieved from a stored set of medical condition evaluation models. That is, each medical condition may have its own separate set of factors that have been learned or specified by subject matter experts, to be relevant to the evaluation of the probability of the medical condition being present. The various evidential information may be categorized into a plurality of different categories of medical concepts, e.g., medical condition code/indicator (e.g., insomnia), anxiety and depression, joint disorder, facts, sleep medications, sleep disorders, psychiatric disorders, etc.

In one illustrative embodiment, the evidential information may be categorized into these various categories by the risk scoring engine 124 such that a count of instances of each category relevant to the evaluation of the particular medical condition may be generated. These counts may be used along with a learned formula or equation to generate a probability score or risk score for the medical condition. For example, for an insomnia medical condition, an equation such as that in equation (1) above may be utilized to generate a value representing the weighted combination of factors. This weighted combination of factors may then be used with equation (2) above to generate a risk score or probability that the medical condition is present in the patient, e.g., a probability that the patient has insomnia.

The resulting risk score or probability may be classified into a plurality of different classifications by the risk scoring engine 124. For example, the risk scoring engine 124 may compare the risk score or probability value to one or more threshold values and/or may generate a ranked listing of medical conditions for the patient. For example, there may be a threshold value defined that indicates a probability value or risk score that indicates that the patient has the corresponding medical condition. Another threshold value may be established to determine a minimum risk score or probability value to indicate a relevant level of risk of the medical condition to warrant ranking and notification of the risk to a physician or other medical personnel. Other thresholds may be established for categorizing the risk score or probability value into different levels of risk including, for example, very high risk, high risk, moderate risk, low risk, or very low risk.

The annotation engine 125 may further annotate the patient EMR by annotating the instances of medical codes or other medical condition indicators in the patient EMR to identify the corresponding risk score, categorization of the risk score or probability value, or the like. In some cases, annotations may be added to make explicit in the patient EMR the disambiguated natural of the medical conditions determined to be present in the patient, e.g., "The patient has hypertension and diabetes type 2."

The results generated by the risk scoring engine 124 may be provided back to the cognitive system 100 for further processing by the cognitive system 100 to perform other decision support cognitive operations, e.g., patient diagnostics, treatment recommendation, patient monitoring, etc. For example, the determination of risk scores and corresponding risk categorizations for various medical conditions may be used as a basis for determining a diagnosis for a patient, e.g. the patient having the particular medical conditions, or a potential reason for another symptom being present in the patient. In some cases, the risk score or risk categorization may be used to generate a treatment recommendation for the patient for recommending a particular medication to be taken by the patient, a particular activity to be performed by the patient, or the like. Various other factors may be cognitively evaluated by the cognitive system 100 and/or pipeline 108, in addition to the risk score, risk categorization, etc. generated by the medical condition verification system 120.

In addition, or alternatively, the medical condition verification system 120 may provide the results of the risk scoring engine 124 to a graphical user interface (GUI) engine 126 which may generate a GUI for presenting information about the medical condition of the patient and/or the patient's risks for particular medical conditions and the reasons for the determination of such risks. This will allow a physician or other medical personnel to utilize the GUI to access information that assists the physician in understanding the medical condition of the patient and the potential risks that the patient may have with regard to various medical conditions.

As discussed previously, the risk scoring engine 124 may be trained to learn the appropriate combination of factors and weightings to be applied to these factors when evaluating a patient's probability of having specific medical conditions, where each medical condition may have a separate specific function for combining and weighting the factors to evaluate the risk score or probability of the patient having the medical condition. The training may be based on a pool of training patient EMRs for patients where it is known what medical conditions the patient has, and which patients do not in fact have the medical conditions. Thus, the training of the risk scoring engine 124 may comprise identifying, from a pool of patients, which patients actually have a particular medical condition, e.g., a particular type of cancer, and which do not have the medical condition, even if the patient's EMRs contain indicators that may be interpreted as indicating that the patient has the medical condition. The mechanisms of the illustrative embodiments may have an initial set of factors specified by subject matter experts (SMEs), extracted from natural language processing of electronic documents specifying medical knowledge in the corpus 140, or the like, and may learn the weightings to be applied to these factors. Moreover, in some illustrative embodiments, patients may be correlated into cohorts and their associated characteristics may be compared to identify characteristics shared amongst patients having the same medical condition. Based on such correlations, new combinations of factors may be learned as being indicative of a medical condition for use in verifying the medical code/indicator.

For example, from a large set of patient EMRs, a pool of patients may be generated that have indicators, e.g., medical codes, indicative of a particular medical condition, e.g., particular type of cancer patients, type 2 diabetes patients, insomnia patients, etc. The mechanisms of the illustrative embodiments learn, from natural language processing of guidelines documents, medical publications, information provided by subject matter experts (SMEs), and the like, the patient characteristics that are supportive and/or not supportive of the hypothesis that the patient has the medical condition indicated by the medical code or other indicator of the medical condition. For example, through an ingestion of such electronic documents, various factors may be identified that are relevant to a particular medical condition, e.g., particular medical codes, patient demographics, comorbidities, medications, related medical concepts, and natural language terms/phrases associated with the medical condition or related medical concepts may be learned through a natural language processing and ingestion of the medical knowledge from these electronic documents.

Various structured and unstructured covariates may be learned by the risk scoring engine 124 to be relevant to the evaluation of the presence of a particular medical condition. As noted above, the particular combination of structured and unstructured covariates applicable to a particular medical condition may differ substantially from the combination of covariates used to evaluate other medical conditions. During training, an evaluation of these characteristics with regard to each of the patients in the pool of patients is performed to determine a likelihood that the patient actually has the medical condition indicated or the medical coding or other indicator is likely associated with a related concept rather than the actual medical condition itself. The risk score, or probability value, generated by evaluating these characteristics, or factors, may be compared to a ground truth for the particular patient in the pool of patients, to determine if the medical condition verification system has correctly or incorrectly identified the particular patient as having the particular medical condition. In response to an error being present a machine learning process is employed to adjust the operational parameters, e.g., weights associated with different structured/unstructured covariates, of the risk scoring engine 124 to reduce the error and increase the accuracy in the risk score calculations. Thus, through the machine learning and training of the risk scoring engine 124, using a training pool of patients, some of which may have the medical condition, and some of which may not have the medical condition, the risk scoring engine 124 is trained to identify structured and unstructured characteristics in a patient's EMR that may be used to verify, or even invalidate, the presence of a medical condition with regard to the patient as indicated by a medical code or other indicator in the patient EMR as well as learns the particular level of influence each of these characteristics or factors have in such a determination of a validity of the medical condition being present, e.g., the weights to be applied to the various characteristics or factors.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 2 is provided as an example of one type of data processing system in which aspects of the present invention may be implemented. Many other types of data processing systems may be likewise configured to specifically implement the mechanisms of the illustrative embodiments.

FIG. 2 is a block diagram of an example data processing system in which aspects of the illustrative embodiments are implemented. Data processing system 200 is an example of a computer, such as a server 104A-D or client 110 in FIG. 1, in which computer usable code or instructions implementing the processes for illustrative embodiments of the present invention are located. In one illustrative embodiment, FIG. 2 represents a server computing device, such as a server 104A-D, which, which implements a cognitive system 100 and QA system pipeline 108 augmented to include the additional mechanisms of the illustrative embodiments described hereafter.

In the depicted example, data processing system 200 employs a hub architecture including North Bridge and Memory Controller Hub (NB/MCH) 202 and South Bridge and Input/Output (I/O) Controller Hub (SB/ICH) 204. Processing unit 206, main memory 208, and graphics processor 210 are connected to NB/MCH 202. Graphics processor 210 is connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE) or serial advanced technology attachment (SATA) interface. Super I/O (SIO) device 236 is connected to SB/ICH 204.

An operating system runs on processing unit 206. The operating system coordinates and provides control of various components within the data processing system 200 in FIG. 2. As a client, the operating system is a commercially available operating system such as Microsoft® Windows 10®. An object-oriented programming system, such as the Java™ programming system, may run in conjunction with the operating system and provides calls to the operating system from Java™ programs or applications executing on data processing system 200.

As a server, data processing system 200 may be, for example, an IBM® eServer™ System p° computer system, running the Advanced Interactive Executive) (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and are loaded into main memory 208 for execution by processing unit 206. The processes for illustrative embodiments of the present invention are performed by processing unit 206 using computer usable program code, which is located in a memory such as, for example, main memory 208, ROM 224, or in one or more peripheral devices 226 and 230, for example.

A bus system, such as bus 238 or bus 240 as shown in FIG. 2, is comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, includes one or more devices used to transmit and receive data. A memory may be, for example, main memory 208, ROM 224, or a cache such as found in NB/MCH 202 in FIG. 2.

Those of ordinary skill in the art will appreciate that the hardware depicted in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

FIG. 3 is an example diagram illustrating an interaction of elements of a healthcare cognitive system in accordance with one illustrative embodiment. The example diagram of FIG. 3 depicts an implementation of a healthcare cognitive system 300 that is configured to provide a medical condition risk graphical user interface either alone or in combination with one or more other graphical user interfaces usable by a physician or other medical personnel. However, it should be appreciated that this is only an example implementation and other healthcare operations may be implemented in other embodiments of the healthcare cognitive system 300 without departing from the spirit and scope of the present invention.

Moreover, it should be appreciated that while FIG. 3 depicts the patient 302 and user 306 as human figures, the interactions with and between these entities may be performed using computing devices, medical equipment, and/or the like, such that entities 302 and 306 may in fact be computing devices, e.g., client computing devices. For example, the interactions 304, 314, 316, and 330 between the patient 302 and the user 306 may be performed orally, e.g., a doctor interviewing a patient, and may involve the use of one or more medical instruments, monitoring devices, or the like, to collect information that may be input to the healthcare cognitive system 300 as patient attributes 318. Interactions between the user 306 and the healthcare cognitive system 300 will be electronic via a user computing device (not shown), such as a client computing device 110 or 112 in FIG. 1, communicating with the healthcare cognitive system 300 via one or more data communication links and potentially one or more data networks.

As shown in FIG. 3, in accordance with one illustrative embodiment, a patient 302 presents symptoms 304 of a medical condition to a user 306, such as a physician or other healthcare practitioner, technician, or the like. The user 306 may interact with the patient 302 via a question 314 and response 316 exchange where the user gathers more information about the patient 302, the symptoms 304, and the medical condition of the patient 302. It should be appreciated that the questions/responses may in fact also represent the user 306 gathering information from the patient 302 using various medical equipment, e.g., blood pressure monitors, thermometers, wearable health and activity monitoring devices associated with the patient such as a FitBit™, a wearable heart monitor, or any other medical equipment that may monitor one or more medical characteristics of the patient 302. In some cases, such medical equipment may be medical equipment typically used in hospitals or medical centers to monitor vital signs and medical conditions of patients that are present in hospital beds for observation or medical treatment.

Either prior to, at substantially a same time, or even after, encountering the patient 302, he user (e.g., physician) 306 submits a request 308 to the healthcare cognitive system 300, such as via a user interface on a client computing device that is configured to allow users to submit requests to the healthcare cognitive system 300 in a format that the healthcare cognitive system 300 can parse and process. The request 308 may include, or be accompanied with, information identifying patient attributes 318. These patient attributes 318 may include, for example, an identifier of the patient 302 from which patient EMRs 322 for the patient may be retrieved, demographic information about the patient, the symptoms 304, and other pertinent information obtained from the responses 316 to the questions 314 or information obtained from medical equipment used to monitor or gather data about the condition of the patient 302. Any information about the patient 302 that may be relevant to a cognitive evaluation of the patient by the healthcare cognitive system 300 may be included in the request 308 and/or patient attributes 318.

The healthcare cognitive system 300 provides a cognitive system that is specifically configured to perform an implementation specific healthcare oriented cognitive operation. In the depicted example, this healthcare oriented cognitive operation is directed to providing a patient EMR GUI 318 which may include a medical condition risk interface with which the user 306 may interact 328, to thereby assist the user 306 in treating the patient 302 based on their reported symptoms 304 and other information gathered about the patient 302 via the question 314 and response 316 process and/or medical equipment monitoring/data gathering. The patient EMR GUI 318 preferably includes the medical condition risk interface as a sub-GUI that is accessed by way of a selectable element of the patient EMR GUI 318 such that the user 306 may view the patient's 302 current medical conditions and risks for other medical conditions, with corresponding risk levels, and supporting evidence for the categorization of the risk for the various medical conditions. These medical conditions in the medical condition risk interface sub-GUI are specifically tied to medical codes or medical condition indicators found in the patient EMR with the risk scores or risk levels being determined through the operation of the medical condition verification system 120 which verifies the instances of medical codes/indicators as being representative of the actual medical condition being present or such instances being directed to related concepts and not necessarily indicating the medical condition being present. For those that are determined not be directed to related concepts, these related concepts are evidence of a risk score or risk level for the related medical condition even though the medical condition itself is not specifically identified by the medical code/indicator.

The healthcare cognitive system 300 operates on the request 308 and patient attributes 318 utilizing information gathered from the medical corpus and other source data 326, treatment guidance data 324, and the patient EMRs 322 associated with the patient 302 to generate patient information that may be output in the patient EMR GUI 318 and the medical condition risk interface sub-GUI with which the user 306 may interact 328. The medical condition risk interface may list the medical conditions that the patient 302 is at risk of having in a ranked ordering with associated supporting evidence, obtained from the patient attributes 318 and data sources 322-326, indicating the reasoning as to why the risk scores or risk levels are determined to be what they are by the medical condition verification system 120. In addition to the healthcare cognitive system 300 operating on the request 308, the For example, based on the request 308 and the patient attributes 318, the healthcare cognitive system 300 may operate on the request, such as by using a request processing pipeline type processing as described herein, to parse the request 308 and patient attributes 318 to determine what is being requested and the criteria upon which the request is to be generated as identified by the patient attributes 318, and may perform various operations for generating queries that are sent to the data sources 322-326 to retrieve data, generate candidate medical conditions based on medical codes/indicators present in the patient's EMR data, and score these candidate medical conditions based on supporting evidence found in the data sources 322-326 to thereby generate a risk score or probability value indicating a probability or risk that the patient has the medical condition.

In the depicted example, the patient EMRs database 322 is a patient information repository that collects patient data from a variety of sources, e.g., hospitals, laboratories, physicians' offices, health insurance companies, pharmacies, etc. The patient EMRs 322 store various information about individual patients, such as patient 302, in a manner (structured, unstructured, or a mix of structured and unstructured formats) that the information may be retrieved and processed by the healthcare cognitive system 300. This patient information may comprise various demographic information about patients, personal contact information about patients, employment information, health insurance information, laboratory reports, physician reports from office visits, hospital charts, historical information regarding previous diagnoses, symptoms, treatments, prescription information, etc. Based on an identifier of the patient 302, the patient's corresponding EMRs 322 from this patient repository may be retrieved by the healthcare cognitive system 300 and searched/processed by cognitive system 300 and the medical condition verification system 120 to generate the patient EMR GUI 318 with the medical condition risk interface with which the user 306 may interact 328 to view specific medical conditions the patient is determined to have and which ones the patient EMR indicates the patient 302 may be at risk of having, potentially ranked in terms of risk score or risk level.

The treatment guidance data 324 provides a knowledge base of medical knowledge that is used to identify potential medical conditions present in a patient based on the patient's attributes 318 and historical information presented in the patient's EMRs 322. This treatment guidance data 324 may be obtained from official treatment guidelines and policies issued by medical authorities, e.g., the American Medical Association, may be obtained from widely accepted physician medical and reference texts, e.g., the Physician's Desk Reference, insurance company guidelines, or the like. The treatment guidance data 324 may be provided in any suitable form that may be ingested by the healthcare cognitive system 300 including both structured and unstructured formats.

The various medical knowledge resources 324, 326 may be processed by the medical condition verification system 120 to evaluate instances of medical codes/indicators in the patient EMR retrieved from the patient EMR database 322 to identify instances that specifically identify a particular medical condition that the patient 302 has, and other instances where the instance of the medical code/indicator is directed to a related concept rather than specifically identifying the medical condition as being present in the patient 302. The medical condition verification system 120 operates in a manner as previously described above with regard to one or more of the illustrative embodiments. The medical condition verification system 120 receives the patient EMR and operates on it using the medical knowledge extracted from the resources 324, 326 and using the learned factors and weightings for the particular medical conditions associated with medical codes/indicators in the patient EMR. The medical condition verification system 120 then returns a disambiguated patient EMR and the medical condition risk interface sub-GUI to the healthcare cognitive system 300. The disambiguated patient EMR comprises annotations that may specify whether or not instances of medical codes/indicators are specifically identifying the medical condition or a related concept. In addition, these annotations may include the determined risk score or risk level categorization for the medical condition associated with the instance of the medical code/indicator. The medical condition risk interface may comprise a natural language statement of the patient's identified medical conditions that the patient has, as well as a listing of the determined risks of medical conditions the patient has based on the evaluation performed by the medical condition verification system 120.

While FIG. 3 is depicted with an interaction between the patient 302 and a user 306, which may be a healthcare practitioner such as a physician, nurse, physician's assistant, lab technician, or any other healthcare worker, for example, the illustrative embodiments do not require such. Rather, the patient 302 may interact directly with the healthcare cognitive system 300 without having to go through an interaction with the user 306 and the user 306 may interact with the healthcare cognitive system 300 without having to interact with the patient 302. For example, in the first case, the patient 302 may be requesting 308 a patient EMR GUI 318 with which the patient 302 may interact 328 directly. Moreover, the healthcare cognitive system 300 may actually have logic for automatically posing questions 314 to the patient 302 and receiving responses 316 from the patient 302 to assist with data collection for generating the patient EMR GUI 318. In the latter case, the user 306 may operate based on only information previously gathered and present in the patient EMR 322 by sending a request 308 along with patient attributes 318 and obtaining the patient EMR GUI in response from the healthcare cognitive system 300. Thus, the depiction in FIG. 3 is only an example and should not be interpreted as requiring the particular interactions depicted when many modifications may be made without departing from the spirit and scope of the present invention. It should be appreciated that the healthcare cognitive system 300 performs decision support cognitive operations and does not in itself provide the treatment itself to the patient 302 without prior approval of the healthcare professional treating the patient, i.e. final determinations as to treatments given to a patient will always fall on the healthcare professional with the mechanisms of the illustrative embodiments serving only as an advisory tool for the healthcare professional (user 306) and/or patient 302.

As noted above, in evaluating the instances of medical codes/indicators in the patient EMR, the medical condition verification system 120 may evaluate evidence in the patient EMR and other sources of patient information according to medical knowledge ingested from medical resources available in one or more corpora. This evaluation may include both natural language processing reasoning algorithms 122 and cognitive analytics 123. With regard to natural language processing, the NLP reasoning algorithms 122 may look for instances of terms/phrases in natural language of the patient EMR and/or other patient information obtained from various patient information sources, such as pharmacy systems, medical laboratory systems, medical equipment supplier systems, and the like, based on knowledge of the terms/phrases that are relevant to the identification of the presence of the actual medical condition with the patient. For example, FIGS. 4A-4C illustrate various phrases associated with different types of medical conditions.

Figure 4A:
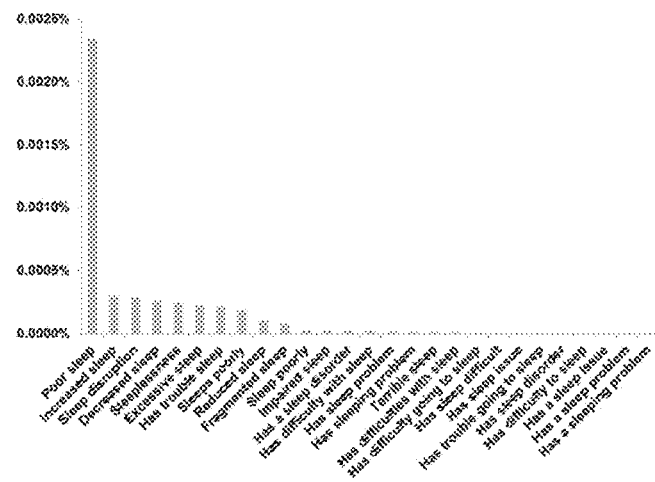
FIGS. 4A-4C illustrate various phrases associated with different types of medical conditions which may serve as a basis for verifying medical codes or medical condition indicators using natural language processing in accordance with one illustrative embodiment.
Figure 4B:
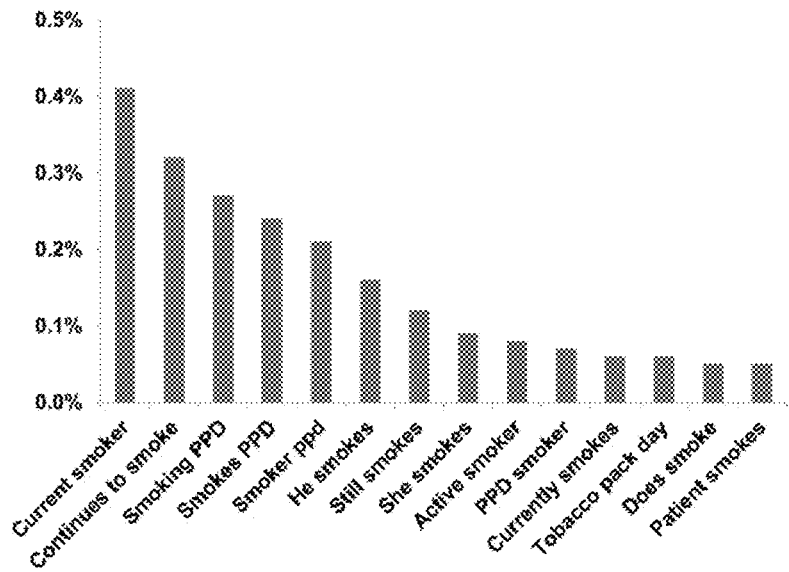
Figure 4C:
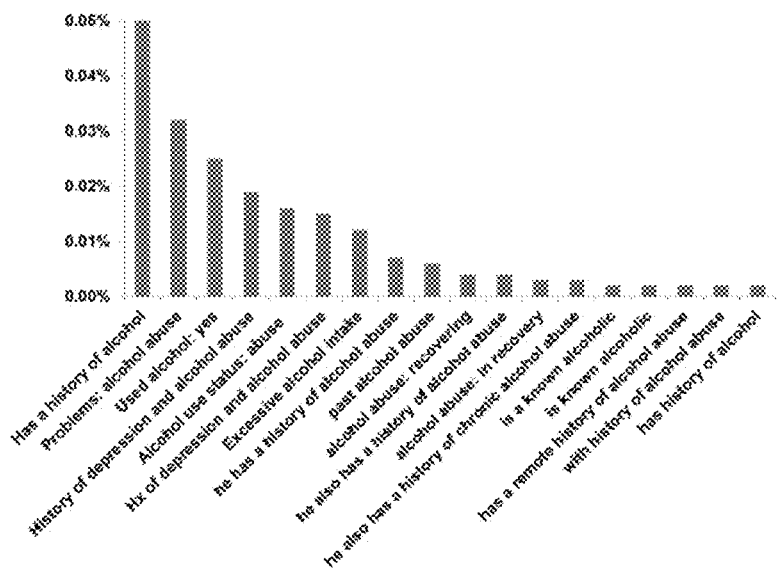

FIG. 4A shows phrases that are often used by physicians and medical personnel when documenting a patient's medical condition of a sleep disorder. FIG. 4B shows phrases that are often used by physicians and medical personnel when documenting a patient's medical condition with regard to smoking status. FIG. 4C shows phrases that are often used by physicians and medical personnel when documenting a patient's alcohol use. The presence of such phrases in a patient's EMR along with a medical code or indicator of the corresponding medical condition, e.g., a medical code for smoker, alcohol user, or sleep disorder, provides evidence that the medical code or medical condition indicator is in fact referring to the actual medical condition being present rather than referring to a related concept and not the medical condition itself. Thus, the occurrence of such phrases may be identified through the NLP reasoning algorithms 122 and the number of such instances, for example, may be used as evidential support for the medical code/indicator being a reference to the actual medical condition itself.

As noted above, the medical condition verification system 120 may generate a medical condition risk graphical user interface, or sub-GUI which may be part of a patient EMR GUI which is accessible via a GUI element present in the patient EMR GUI. FIGS. 5A and 5B illustrate an example of a patient EMR GUI that may be generated by the cognitive system including a GUI element 560 for accessing a sub-GUI, or the medical condition risk interface, which is shown in FIG. 5B in accordance with one illustrative embodiment.

With reference to FIG. 5A, the patient EMR GUI comprises a relevant information graphical user interface (GUI) 500 that highlights information for summarizing the relevant patient information for answering the prototypical questions that a physician or other medical personnel may ask when reviewing the patient's health condition in an effort to treat the patient. The GUI 500 may include links to the source of the information represented in the GUI in addition to comprising natural language text descriptions, graphical representations, and the like, to represent the relevant information in an organized and accessible manner for human consumption.

As shown in FIG. 5A, the patient EMR GUI 500 includes a history portion 510 for treating a particular patient. History portion 510 presents a history timeline with indicators for encounters between the physician, or other medical personnel, and the patient. The encounters may include primary care physician office visits, hospital visits, a current encounter with the patient, and the like. Thus, the information aggregated and synthesized within GUI 500 is presented within a consistent timeline based on history portion 510.

Outcome portion 520 presents the outcome the physician is attempting to measure or control, graphed along a historical timeline. Supporting measurements portion 530 presents the measurements that support what the physician is doing to control the outcome. Lifestyle portion 540 presents lifestyle information if the doctor is using lifestyle changes to control the condition or outcome. Ancillary measurements portion 550 presents measurements that are related to the outcome of interest. All this information is overlaid along a consistent timeline in this illustrative embodiment so as to make the representation of patient information consistent and organized for ease of correlation and ingestion by the human user, e.g., the physician or other medical personnel.

GUI portion 501 presents answers to other prototypical questions, such as the plan from the last visit, events that happened since the last visit, to-do lists that are guideline based for the particular disease and correlate with information in the EMR to determine if the patient is complying with these to-do items and to check if the patient has scheduled appointments and such. In the example depicted in FIG. 5A, GUI portion 501 presents an answer to a prototypical question concerning a plan from the last visit.

In addition to these elements, the GUI 500 further includes a GUI element 560 (in this case a virtual button, but not being limited to such) for accessing a medical condition risk interface, referred to in FIG. 5A as the "Diseases at Risk" sub-GUI. The "Diseases at Risk" sub-GUI is generated using the results generated by the medical condition verification system 120 which verifies the instances of medical codes or medical condition indicators in the patient EMR, generates risk scores or probability values for the various medical conditions potentially indicated by the medical codes or medical condition indicators, and annotates the patient EMR to identify which medical codes/indicators are referencing the medical condition itself and which are associated with related concepts that give rise to a risk score or probability value of the associated medical condition.

FIG. 5B is an example diagram of the "Diseases at Risk" sub-GUI which may be output to the user in response to the user selecting the "Diseases at Risk" GUI element 560 in FIG. 5A. As shown in FIG. 5B, the sub-GUI comprises a patient summary portion 570 that summarizes the demographics of the patient and the currently known medical conditions of the patient. In particular, this summary may include an identification of the medical conditions whose risk scores or probability values, generated by the medical condition verification system 120, that equal or exceed a threshold value that is indicative of the patient actually having the medical condition. In the depicted example, the patient summary portion 570 indicates that the patient, George, is a 52-year-old male, as indicated from the patient EMR data. In addition, the summary 570 further lists the medical conditions of the patient as verified by the medical condition verification system 120, i.e. Hypertension, Diabetes, and Post MI. From the patient's EMR data, the patient summary portion 570 may further list the current medications and dosages that the patient is taking, i.e. Losartan 50 mg and Atenolol 50 mg, as well as other characteristics of the patient that may be important to highlight to the physician or other medical personnel, such as allergies and the like.

The sub-GUI further includes a listing of medical conditions that the patient is at risk of having based on the risk evaluation performed by the medical condition verification system 120. The listing may include a designation of the medical condition 580, a risk level 590 determined based on the risk score or probability value generated by the medical condition verification system 120, and a listing of reasons 595 supporting the designation of the risk level. The risk level may be a categorization of the risk score into one of a plurality of predefined risk levels as previously described above, based on the risk score being generated using a learned relationship of factors, such as represented in equations (1) and (2) above for example. The reason 595 may be a natural language statement as to the factors that were found to be most influential in the generation of the risk score and thus, the categorization into the corresponding risk level 590. The listing may comprise those medical conditions associated with medical codes or medical condition identifiers in the patient EMR data which have a sufficient amount of evidential information in the other portions of the EMR data and/or other patient information from other patient information sources, to provide a minimum level of evidential support that the patient has a risk of having the associated medical condition. With the "Diseases at Risk" sub-GUI, the physician is able to see quickly the medical conditions that the patient has, as well as the medical conditions the patient is at risk of having and the level of such risk, as well as understand the reasons why the patient is determined to have such risks. All of this information assists the physician in interacting with the patient during an encounter and obtaining a holistic view of the patient's health so as to best treat the patient for the medical conditions that the patient has and attempt to reduce the level of risk the patient has for other medical conditions indicated in the listing.

Figure 6:
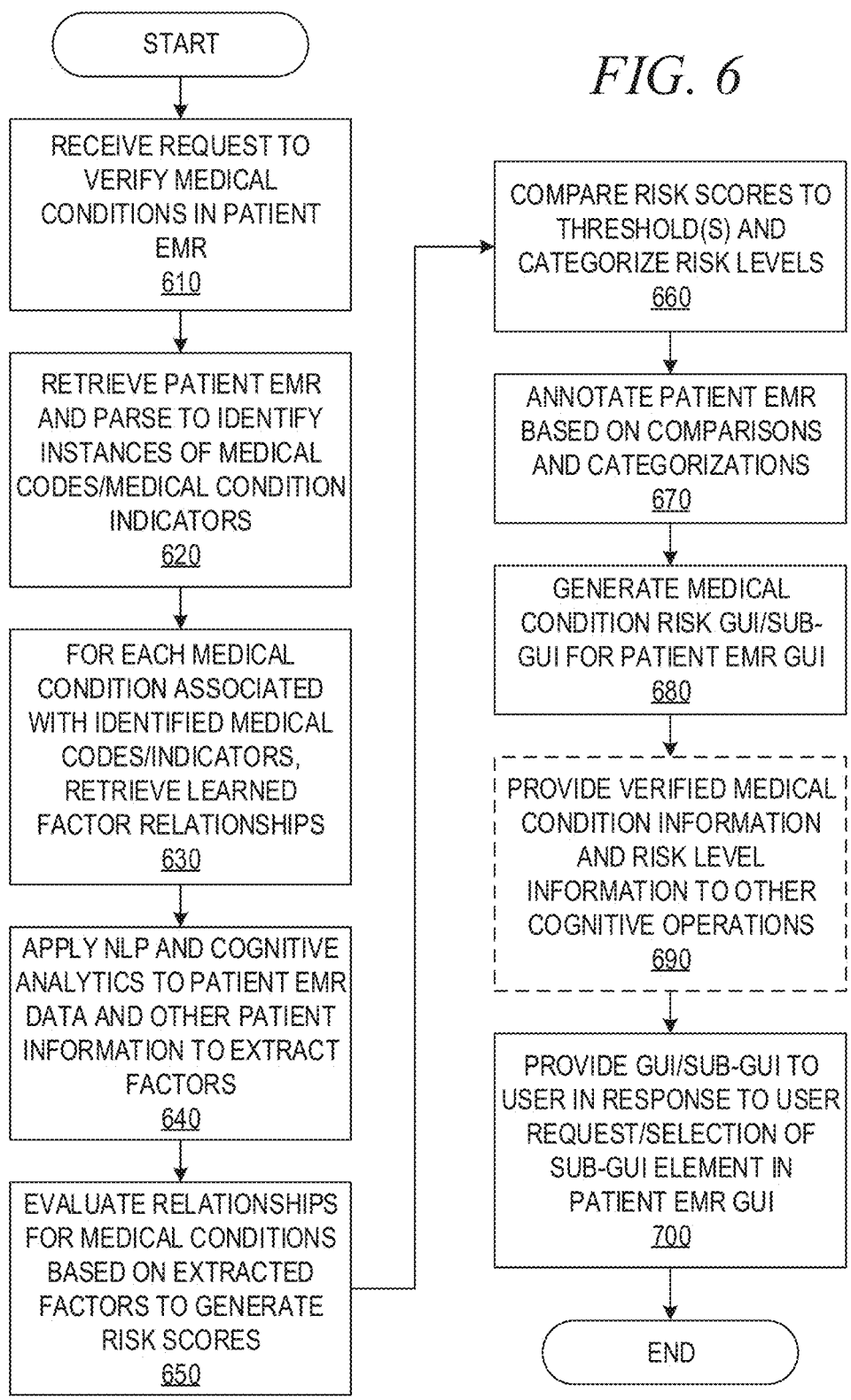
FIG. 6 is a flowchart outlining an example operation for verifying medical conditions indicated by a patient's EMR in accordance with one illustrative embodiment.

FIG. 6 is a flowchart outlining an example operation for verifying medical conditions indicated by a patient's EMR in accordance with one illustrative embodiment. The operation outlined in FIG. 6 may be implemented, for example, by the medical condition verification system 120 of FIG. 1. As shown in FIG. 6, the operation starts by receiving a request to verify the medical conditions in a patient's EMR data (step 610). The patient EMR is retrieved and parsed to identify instances of medical codes/medical condition indicators (step 620). For each medical condition associated with an identified medical code/indicator, the learned factor relationships associated with the medical condition is retrieved (step 630). The factor relationships are learned using a machine learning approach as previously described above which may involve learning the factors themselves and/or learning the weightings to be applied to the various factors to evaluate a risk score or probability value that the medical condition is actually present in the patient and thus, the medical code/indicator is in fact referencing the actual medical condition and not just a related concept.

Natural language processing reasoning algorithms and/or cognitive analytics are applied to the patient EMR data and other patient information to extract the factors, or evidential information, for evaluating the retrieved relationships (step 640). The relationships for the medical conditions are evaluated based on the extracted factors to thereby generate risk scores or probability values that the patient has the medical condition or is at risk of having the medical condition (step 650). The risk scores are compared to threshold(s) and are categorized into risk levels (step 660). The comparison against threshold(s) allows for the identification of medical conditions that the patient is determined to have, medical conditions that the patient is at risk of having, and medical conditions for which there is not sufficient other evidential support that the patient has a risk of having.

The patient EMR data may then be annotated based on the results of the comparisons to thresholds and the categorizations of the risk levels (step 670). A medical condition risk GUI may be generated, or a sub-GUI that may be included with a patient EMR GUI (step 680). Optionally, the verified medical condition information and risk level information may be provided to other cognitive operations which utilize them to at least partially perform other cognitive operations, such as patient diagnosis, treatment recommendations, patient monitoring, and other decisions support cognitive operations (step 690). The medical condition risk GUI/sub-GUI is provided to the user in response to a user request or selection of a sub-GUI element in the patient EMR GUI (step 700). The operation then terminates.

Thus, the illustrative embodiments provide mechanisms for verifying medical conditions of patients indicated in medical codes and/or other medical condition indicators in their patient EMR data. The illustrative embodiments determine a risk score, or probability value, of each medical condition indicated based on an evaluation of other evidential support that supports a finding that the medical code or indicator is in fact referencing the medical condition and not a related medical concept. The risk score or probability value is an indicator of a likelihood that the patient has the corresponding medical condition. Based on the risk score or probability value, a determination as to whether the patient actually has the corresponding medical condition or not may be determined. Moreover, for those medical conditions that are not considered to have a sufficiently high risk score or probability value to make a determination that the patient actually has the medical condition, the medical conditions may be evaluated based on a determined level of risk that the patient has for having the medical condition. The risk levels may be ranked relative to one another and the medical condition information may be used to annotate the patient EMR data, as input to other cognitive operations, and/or output in a graphical user interface for use by a physician or other medical personnel.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, the at least one memory comprising instructions executed by the at least one processor to cause the at least one processor to implement a medical condition verification system, the method comprising:

training, via a machine learning process, the medical condition verification system to learn a machine learned relationship of medical factors in patient electronic medical record (EMR) data relevant to generating a measure of risk for the associated medical condition, wherein the training is performed on a plurality of training patient EMR data structures, each training patient EMR data structure in the plurality of training patient EMR data structures having a same medical code present in the training patient EMR data structure, and wherein the machine learned relationship differentiates first instances of the same medical code in training patient EMR data structures for patients where the first instances represent that the patient actually has a corresponding medical condition from second instances of the same medical code in training patient EMR data structures for patients where the second instances of the same medical code represent a related concept related to the corresponding medical condition but does not represent that the patient has the corresponding medical condition;

parsing, by the medical condition verification system, received patient EMR data to identify a third instance of the medical code present in the received patient EMR data;

performing, by the medical condition verification system, cognitive analysis of the received patient EMR data to identify evidential data supportive of the instance referencing the corresponding medical condition;

generating, by the medical condition verification system, for the third instance of the medical code, a measure of risk of the patient having the corresponding medical condition based on the identified evidential data and based on the machine learned relationship; and modifying, by the medical condition verification system, based on the measure of risk, the received patient EMR data to comprise at least one annotation data element associated with the third instance of the medical code in the received patient EMR data to thereby generate modified patient EMR data, wherein the annotation data element specifies whether the measure of risk indicates that the patient corresponding to the received patient EMR data has the corresponding medical condition or the third instance represents a related concept to the medical condition but not the medical condition.

2. The method of claim 1, wherein the machine learning further comprises performing natural language processing on the electronic documents in the corpus of electronic documents to extract the medical factors.

3. The method of claim 1, further comprising generating an output representing the measure of risk of the patient having the associated medical condition at least by comparing the measure of risk to one or more threshold values, and wherein in response to the measure of risk being equal to or above a first threshold value in the one or more threshold values, generating a first annotation data element for inclusion in the received patient EMR data indicating that the patient has the corresponding medical condition.

4. The method of claim 3, wherein in response to the measure of risk being equal to or lower than a second threshold value in the one or more threshold values, generating a second annotation data element for inclusion in the received patient EMR data indicating that the patient does not have the associated medical condition.

5. The method of claim 3, wherein generating the output comprises:

generating a graphical user interface having a description of medical conditions associated with medical codes in the received patient EMR data, for which associated measures of risk are equal to or above the first threshold value, wherein the description specifies that the patient has the medical conditions.

6. The method of claim 1, wherein generating the output further comprises:

generating a graphical user interface having a ranked listing of medical conditions associated with medical codes in the received patient EMR data, wherein the medical conditions are ranked in the ranked listing of medical conditions according to their associated measures of risk.

7. The method of claim 6, wherein the ranked listing of medical conditions comprises, for each medical condition in the ranked listing, a score value associated with the medical condition indicating a likelihood that the patient has or may develop the medical condition.

8. The method of claim 1, wherein the method is initiated in response to the instance of the medical code being added to the patient EMR data.

9. The method of claim 1, further comprising:
storing, by the medical condition verification system, the modified patient EMR data for performance of cognitive computing operations by cognitive computing systems based on the at least one annotation data element in the modified patient EMR data; and
processing, by a cognitive computing system, the modified patient EMR data based on the annotation data element, to determine at least one of a medical diagnosis or a medical treatment recommendation for the patient.

10. The method of claim 1, wherein the annotation data element comprises a natural language statement specifying whether or not the patient has the corresponding medical condition.

11. A computer program product comprising a computer readable storage medium having a computer readable program stored therein, wherein the computer readable program, when executed on a data processing system, causes the data processing system to implement a medical condition verification system that operates to:
train the medical condition verification system to learn a machine learned relationship of medical factors in patient electronic medical record (EMR) data relevant to generating a measure of risk for the associated medical condition, wherein the training is performed on a plurality of training patient EMR data structures, each training patient EMR data structure in the plurality of training patient EMR data structures having a same medical code present in the training patient EMR data structure, and wherein the machine learned relationship differentiates first instances of the same medical code in training patient EMR data structures for patients where the first instances represent that the patient actually has a corresponding medical condition from second instances of the same medical code in training patient EMR data structures for patients where the second instances of the same medical code represent a related concept related to the corresponding medical condition but does not represent that the patient has the corresponding medical condition;
parse received patient EMR data to identify a third instance of the medical code present in the received patient EMR data;
perform cognitive analysis of the received patient EMR data to identify evidential data supportive of the instance referencing the corresponding medical condition;
generate for the third instance of the medical code, a measure of risk of the patient having the corresponding medical condition based on the identified evidential data and based on the machine learned relationship; and
modify, by the medical condition verification system, based on the measure of risk, the received patient EMR data to comprise at least one annotation data element associated with the third instance of the medical code in the received patient EMR data to thereby generate modified patient EMR data, wherein the annotation data element specifies whether the measure of risk indicates that the patient corresponding to the received patient EMR data has the corresponding medical condition or the third instance represents a related concept to the medical condition but not the medical condition.

12. The computer program product of claim 11, wherein the machine learning further comprises performing natural language processing on the electronic documents in the corpus of electronic documents to extract the medical factors.

13. The computer program product of claim 11, wherein the computer readable program further causes the medical condition verification system to generate an output representing the measure of risk of the patient having the associated medical condition at least by comparing the measure of risk to one or more threshold values, and wherein in response to the measure of risk being equal to or above a first threshold value in the one or more threshold values, generate a first annotation data element for inclusion in the received patient EMR data indicating that the patient has the corresponding medical condition.

14. The computer program product of claim 13, wherein in response to the measure of risk being equal to or lower than a second threshold value in the one or more threshold values, generate a second annotation data element for inclusion in the received patient EMR data indicating that the patient does not have the associated medical condition.

15. The computer program product of claim 13, wherein the computer readable program further causes the medical condition verification system to generate the output at least by generating a graphical user interface having a description of medical conditions associated with medical codes in the received patient EMR data, for which associated measures of risk are equal to or above the first threshold value, wherein the description specifies that the patient has the medical conditions.

16. The computer program product of claim 11, wherein the computer readable program further causes the medical condition verification system to generate the output at least by:
generating a graphical user interface having a ranked listing of medical conditions associated with medical codes in the received patient EMR data, wherein the medical conditions are ranked in the ranked listing of medical conditions according to their associated measures of risk.

17. The computer program product of claim 16, wherein the ranked listing of medical conditions comprises, for each medical condition in the ranked listing, a score value associated with the medical condition indicating a likelihood that the patient has or may develop the medical condition.

18. The computer program product of claim 11, wherein the computer readable program further causes the medical condition verification system to store the modified patient EMR data for performance of cognitive computing operations by cognitive computing systems based on the at least one annotation data element in the modified patient EMR data, and wherein a cognitive computing system processes the modified patient EMR data based on the annotation data element, to determine at least one of a medical diagnosis or a medical treatment recommendation for the patient.

19. The computer program product of claim 11, wherein the annotation data element comprises a natural language statement specifying whether or not the patient has the corresponding medical condition.

20. An apparatus comprising:
at least one processor; and
at least one memory coupled to the at least one processor, wherein the at least one memory comprises instructions which, when executed by the at least one processor, cause the at least one processor to implement a medical condition verification system that operates to:

train the medical condition verification system to learn a machine learned relationship of medical factors in patient electronic medical record (EMR) data relevant to generating a measure of risk for the associated medical condition, wherein the training is performed on a plurality of training patient EMR data structures, each training patient EMR data structure in the plurality of training patient EMR data structures having a same medical code present in the training patient EMR data structure, and wherein the machine learned relationship differentiates first instances of the same medical code in training patient EMR data structures for patients where the first instances represent that the patient actually has a corresponding medical condition from second instances of the same medical code in training patient EMR data structures for patients where the second instances of the same medical code represent a related concept related to the corresponding medical condition but does not represent that the patient has the corresponding medical condition;

parse received patient EMR data to identify a third instance of the medical code present in the received patient EMR data;

perform cognitive analysis of the received patient EMR data to identify evidential data supportive of the instance referencing the corresponding medical condition;

generate for the third instance of the medical code, a measure of risk of the patient having the corresponding medical condition based on the identified evidential data and based on the machine learned relationship; and modify, by the medical condition verification system, based on the measure of risk, the received patient EMR data to comprise at least one annotation data element associated with the third instance of the medical code in the received patient EMR data to thereby generate modified patient EMR data, wherein the annotation data element specifies whether the measure of risk indicates that the patient corresponding to the received patient EMR data has the corresponding medical condition or the third instance represents a related concept to the medical condition but not the medical condition.

* * * * *